United States Patent
Cordell et al.

(10) Patent No.: US 6,713,276 B2
(45) Date of Patent: Mar. 30, 2004

(54) MODULATION OF Aβ LEVELS BY β-SECRETASE BACE2

(75) Inventors: Barbara Cordell, Palo Alto, CA (US); Frauke Schimmöller, Menlo Park, CA (US); Yu-Wang Liu, Santa Clara, CA (US); Diana Hom Quon, Redwood City, CA (US)

(73) Assignee: Scios, Inc., Fremont, CA (US)

( * ) Notice: Subject to any disclaimer, the term of this patent is extended or adjusted under 35 U.S.C. 154(b) by 67 days.

(21) Appl. No.: 09/886,143

(22) Filed: Jun. 20, 2001

(65) Prior Publication Data

US 2002/0159991 A1 Oct. 31, 2002

Related U.S. Application Data

(60) Provisional application No. 60/215,729, filed on Jun. 28, 2000.

(51) Int. Cl.[7] .................................................. C12Q 1/37
(52) U.S. Cl. ............................ 435/23; 435/24; 435/69.2
(58) Field of Search ............................ 435/23, 24, 69.2

(56) References Cited

U.S. PATENT DOCUMENTS 5,656,477 A * 8/1997 Vitek et al. .................. 435/325
2002/0157122 A1 * 10/2002 Wong et al. .................... 800/12

FOREIGN PATENT DOCUMENTS

| EP | 0 848 062 A2 | 6/1998 |
| WO | WO 99/34004 A3 | 7/1999 |
| WO | WO 99/34004 A2 | 7/1999 |
| WO | WO 01/23533 A2 | 4/2001 |

OTHER PUBLICATIONS

Citron M. Inhibition of Anyloid Beta Protein Production in Neural Cells by the Serine Protease Inhibitor AEBSF. Neuron 17 171–179, Jul. 1996.*
Farzan M. BACE2, a Beta Secretase Homolog . . . PNAS Aug. 15, 2000, 97(17)9712–9717.*
Saunders A. BACE Maps to Chromosome 11 and a BACE Homolog BACE2 . . . Science 286 Nov. 12, 1999, 1255a.*
Selkoe D. PNAS May 23, 2000, 97(11)5690–5692.*
Vassar R. Beta Secretase Cleavage of Alzheimer's Amyloid Precursor Protein by the Transmembrane Aspartic Protease BACE. Science 286(5440)22 Oct. 1999, 735–741.*
Solans A. A New Aspartyl Protease . . . Cytogenetics and Cell Genetics 89(3–4)177–184, 2000.*
Roach A. Inhibition of Alzheimer's Peptide Formation by otent Nonpeptide Gamma Secretase Inhibitors. Abstract 180.21. Soc for Neuroscience 26(1–2)2000.*
Gen Bank accession No. AF050171 *Homo sapiens* aspartly protease mRNA complete cds. No Date Provided.

Acquati, F. et al., "The gene encoding DRAP (BACE2), a glycosylated transmembrane protein of the aspartic protease family, maps to the Down critical region," *FEBS Letters*, vol. 468, pp. 59–64 (2000).
Bennett, B.D. et al., "A Furin–like Convertase Mediates Propeptide Cleavage of BACE, the Alzheimer's β–Secretase," *The Journal of Biological Chemistry*, vol. 275, No. 48, pp. 37712–37717 (2000).
Bennett, B.D. et al., "Expression Analysis of BACE2 in Brain and Peripheral Tissues," *J. Biological Chemistry*, vol. 275, Issue 27, pp. 20647–20651 (2000).
Cai, Xiao–Dan et al., "Release of Excess Amyloid β Protein from a Mutant Amyloid β Protein Precursor," *Science*, vol. 259, pp. 514–516 (1993).
Checler, F., "Processing of the β–Amyloid Precursor Protein and Its Regulation in Alzheimer's Disease," *Journal of Neurochemistry*, vol. 65, No. 4, pp. 1431–1444 (1995).
Citron, M. et al., "Generation of Amyloid β Protein from Its Precursor Is Sequence Specific," *Neuron*, vol. 14, pp. 661–670 (1995).
Citron, M. et al., "Inhibition of Amyloid β–Protein Production in Neural Cells by the Serine Protease Inhibitor AEBSF," *Neuron*, vol. 17, pp. 171–179 (1996).
Citron, M. et al., "Mutation of the β–amyloid precursor protein in familial Alzheimer's disease increases β–protein production," *Nature*, vol. 360, pp. 672–674 (1992).
Clark, R.F. et al., "Molecular Genetics of Alzheimer's Disease," *Arch. Neurol.*, vol. 50, pp. 1164–1172 (1993).
Farzan, M. et al., "BACE2, a β–secretase homolog, cleaves at the β site and within the amyloid–β region of the amyloid–β precursor protein," *PNAS*, vol. 97, No. 17, pp. 9712–9717 (2000).
Glenner, G.G. et al., "Amyloidosis of the nervous system," *Journal of the Neurological Sciences*, vol. 94, pp. 1–28 (1989).
Goodison, K.L. et al., "Neuronal and Glial Gene Expression in Neocortex of Down's Syndrome and Alzheimer's Disease," *Journal of Neuropathology and Experimental Neurology*, vol. 52, No. 3, pp. 192–198 (1993).
Gouras, G.K. et al., "Testosterone reduces neuronal secretion of Alzheimer's β–amyloid peptides," *PNAS*, vol. 97, No. 3, pp. 1202–1205 (2000).
Greenberg, S.M., M.D. et al., "The clinical spectrum of cerebral amyloid angiopathy: presentations without lobar hemorrhage," *Neurology*, vol. 43, pp. 2073–2079 (1993).

(List continued on next page.)

*Primary Examiner*—Ralph Gitomer
(74) *Attorney, Agent, or Firm*—Morrison & Foerster LLP

(57) ABSTRACT

The present invention is based on the findings that BACE 2, a homolog of β-secretase BACE, is able to stimulate processing of APP in a non-amyloidogenic pathway, thereby suppressing the level of Aβ. Accordingly, the present invention provides methods and means for the identification and use of modulators of this unique activity of BACE 2 to suppress Aβ production. The compounds identified using the methods and means provided herein may be used as potential candidates for the treatment of Alzheimer's disease and other neurological diseases.

27 Claims, 8 Drawing Sheets

OTHER PUBLICATIONS

Haan, J. et al., "Amyloid in central nervous system disease," *Clin. Neurol. Neurosurg.*, vol. 92–4, pp. 305–310 (1990).

Haass, C. et al., "The Presenilins in Alzheimer's Disease—Proteolysis Holds the Key," *Science*, vol. 286, pp. 916–919 (1999).

Hardy, J., "Alzheimer's Disease Clinical Molecular Genetics," *Alzheimer's Disease Update*, vol. 10, No. 2, pp. 239–247 (1994).

Hardy, J., "Amyloid, the presenilins and Alzheimer's disease," *TINS*, vol. 20, No. 4, pp. 154–159 (1997).

Hardy, J., "Framing β–amyloid," *Nature Genetics*, vol. 1, pp. 233–234 (1992).

Hattori, M. et al., "The DNA sequence of human chromosome 21," *Nature*, vol. 405, pp. 311–319 (2000).

Higaki, J. et al., "Inhibition of β–Amyloid Formation Identifies Proteolytic Precursors and Subcellular Site of Catabolism," *Neuron*, vol. 14, pp. 651–659 (1995).

Higaki, J. et al., "Processing of β–Amyloid Precursor Protein by Cathepsin D," *The Journal of Biological Chemistry*, vol. 271, No. 50, pp. 31885–31893.

Higaki, J.N. et al., "A Combinatorial Approach to the Identification of Dipeptide Aldehyde Inhibitors of β–Amyloid Production," *J. Med. Chem.*, vol. 42, pp. 3889–3898 (1999).

Hussain, I. et al., "Identification of a Novel Aspartic Protease (Asp 2) as β–Secretase," *Molecular and Cellular Neuroscience*, vol. 14, pp. 419–427 (1999).

Ida, N. et al., "Analysis of Heterogeneous βA4 Peptides in Human Cerebrospinal Fluid and Blood by a Newly Developed Sensitive Western Blot Assay," *The Journal of Biological Chemistry*, vol. 271, No. 37, pp. 22908–22914 (1996).

Itoh, Y. et al., "Cerebral amyloid angiopathy: a significant cause of cerebellar as well as lobar cerebral hemorrhage in the elderly," *Journal of the Neurological Sciences*, vol. 116, pp. 135–141 (1993).

Johnson–Wood, K. et al., "Amyloid precursor protein processing and Aβ$_{42}$ depositin in a transgenic mouse model of Alzheimer disease," *Proc. Natl. Acad. Sci. USA*, vol. 94, pp. 1550–1555 (1997).

Kalaria, R.N. et al., "Differential degeneration of the cerebral microvasculature in Alzheimer's disease," *NeuroReport*, vol. 6, No. 3, pp. 477–480 (1995).

Kang, J. et al., "The precursor of Alzheimer's disease amyloid A4 protein resembles a cell–surface receptor," *Nature*, vol. 325, pp. 733–736 (1987).

Kawai, M. et al., "Degeneration of vascular muscle cells in cerebral amyloid angiopathy of Alzheimer disease," *Brain Research*, vol. 623, pp. 142–146.

Kitaguchi, N. et al., "Novel precursor of Alzheimer's disease amyloid protein shows protease inhibitory activity," *Nature*, vol. 331, pp. 530–532 (1988).

Lannfelt, L. et al., "Amyloid precursor protein gene mutation at codon 670/671 in familial Alzheimer's disese in Sweden," *Biochemical Society Transactions*, vol. 22, pp. 176–179 (1993).

Levy, E. et al., "Mutation of the Alzheimer's Disease Amyloid Gene in Hereditary Cerebral Hemorrhage, Dutch Type," *Science*, vol. 24, pp. 1124–1128 (1990).

Li, Yue–Ming et al., "Presenilin 1 is linked with γ–secretase activity in the detergent solubilized state," *PNAS*, vol. 97, No. 11, pp. 6138–6143 (2000).

Lin, X. et al., "Human aspartic protease memapsin 2 cleaves the β–secretase site of β–amyloid precursor protein," *PNAS*, vol. 97, No. 4, pp. 1456–1460 (2000).

Maat–Schieman, M.L.C. et al., "Hereditary cerebral hemorrhage with amyloidosis (Dutch): a model for congophilic plaque formation without neurofibrillary pathology," *Acta Neuropathologica*, vol. 88, pp. 371–378 (1994).

Mandybur, T.I., "Cerebral amyloid angiopathy and astrocytic gliosis in Alzheimer's disease," *Acta Neuropathologica*, vol. 78, pp. 329–331 (1989).

Mann, D.M.A. et al., "The time course of pathological events in Down's Syndrome with particular reference to the involvement of microglial cells and deposits of β/A4," *Neurodegeneration*, vol. 1, pp. 201–215 (1992).

Martin, L.J. et al., "Synaptic Pathology and Glial Responses to Neuronal Injury Precede the Formation of Senile Plaques and Amyloid Deposits in the Aging Cerebral Cortex," *American Journal of Pathology*, vol. 145, No. 6, pp. 1358–1381 (1994).

Masliah, E. et al., "Comparison of Neurodegenerative Pathology in Transgenic Mice Overexpressing V717F β–Amyloid Precursor Protein and Alzheimer's Disease," *The Journal of Neurosciences*, vol. 16, No. 18, pp. 5795–5811 (1996).

Mullan, M. et al., "A pathogenic mutation for probable Alzheimer's disease in the APP gene at the N–terminus of β–amyloid," *Nature Genetics*, vol. 1, pp. 345–347 (1992).

Oyama, F. et al., "Down's Syndrome: Up–Regulation of β–Amyloid Protein Precursor and τ mRNAs and Their Defective Coordination," *Journal of Neurochemistry*, vol. 62, No. 3, pp. 1062–1066 (1994).

Pike, C.J. et al., "Structure–Activity Analyses of β–Amyloid Peptides: Contributions of the β25–35 Region to Aggregation and Neurotoxicity," *Journal of Neurochemistry*, vol. 64, No. 1, pp. 253–265 (1995).

Ponte, P. et al., "A new A4 amyloid mRNA contains a domain homologous to serine proteinase inhibitors," *Nature*, vol. 331, pp. 525–527 (1988).

Saunders, A.J. et al., "BACE Maps to Chromosome 11 and BACE Homolog, BACE2, Reside in the Obligate Down Syndrome Region of Chromosome 21," *Science*, vol. 286, p. 1255a (1999).

Selkoe, D.J. et al., *PNAS*, vol. 97, No. 11, pp. 5690–5692 (2000).

Selkoe, D.J., "β–Amyloid precursor protein of Alzheimer disease occurs as 110–to 135–kilodation membrane–associated proteins in neural and nonneural tissues," *Proc. Natl. Acad. Sci. USA*, vol. 85, pp.7341–7345 (1988).

Selkoe, D.J., "Amyloid β–Protein and the Genetics of Alzheimer's Disease," *The Journal of Biological Chemistry*, vol. 271, No. 31, pp. 18295–18298 (1996).

Selkoe, D.J., "Physiological production of the β–amyloid protein and the mechanism of Alzheimer's disease," *TINS*, vol. 16, No. 10, pp. 403–409 (1993).

Selkoe, D.J., "Translating cell biology into therapeutic advances in Alzheimer's disease," *Nature*, vol. 399, pp. A23–A31 (1999).

Seubert, P. et al.,"Secretion of β–amyloid precursor protein cleaved at the amino terminus of the β–amyloid peptide," *Letters to Nature*, vol. 361, pp. 260–262 (1993).

Shoji, M. et al., "Production of the Alzheimer Amyloid βProtein by Normal Proteolytic Processing," *Science*, vol. 258, pp. 126–129 (1992).

Sinha, S. et al., "Cellular mechanisms of β–amyloid production and secretion," *Proc. Natl. Acad. Sci. USA*, vol. 96, pp. 11049–11053 (1999).

Sinha, S. et al., "Purification and cloning of amyloid precursor protein β–secretase from human brain," *Letters to Nature*, vol. 402, pp. 537–540 (1999).

Skovronsky, D.M. et al., "Protein Kinase C–dependent α–Secretase Competes with β–Secretase for Cleavage of Amyloid–β Precursor Protein in the Trans–Golgi Network," *The Journal of Biological Chemistry*, vol. 275, No. 4, pp. 2568–2575 (2000).

Tanzi, R.E. et al., "Protease inhibitor domain encoded by an amyloid protein precursor mRNA associated with Alzheimer's disease," *Nature*, vol. 331, pp. 528–530 (1988).

Terry, R.D., M.D. et al., "Structural Basis of the Cognitive Alterations in Alzheimer Disease," *Alzheimer Disease*, edited by R.D. Terry, R. Katzman and K.L. Bick, Raven Press, Ltd., New York (1994), pp. 179–196.

Vassar, R. et al., "β–Secretase Cleavage of Alzheimer's Amyloid Precursor Protein by the Transmembrane Aspartic Protease BACE," *Science*, vol. 286, pp. 735–741 (1999).

Vinters, H.V., "Cerebral Amyloid Angiopathy A Critical Review," *Stroke*, vol. 18, No. 2, pp. 311–324 (1987).

Wattendorff, A.R. et al., "Hereditary cerebral haemorrhage with amyloidosis, Dutch type (HCHWA–D): clinicopathological studies," *Journal of Neurology, Neurosurgery, and Psychiatry*, vol. 58, pp. 699–705 (1995).

Wisniewski, K.E. et al., "Occurrence of Neuropathologica Changes and dementia of Alzheimer's Disease in Down's Syndrome," *Annals of Neurology*, vol. 17, No. 3, pp. 278–282 (1985).

Wolfe, M.S. et al., "A Substrate–Based Difluoro Ketone Selectively Inhibits Alzheimer's γ–Secretase Activity," *J. Med. Chem.*, vol. 41, pp. 6–9 (1998).

Wolfe, M.S. et al., "Two transmembrane aspartates in presenilin–1 required for presenilin endoproteolysis and γ–secretase activity," *Nature*, vol. 398, pp. 513–517 (1999).

Yamada, M. et al., "Subarchnoid hemorrhage in the elderly: a necropsy study of the association with cerebral amyloid angiopathy," *Journal of Neurology, Neurosurgery, and Psychiatry*, vol. 56, pp. 543–547 (1993).

Yan, R. et al., "Membrane–anchored aspartyl protease with Alzheimer's disease β–secretase activity," *Letters to Nature*, vol. 402, pp. 533–537 (1999).

* cited by examiner

Figure 7

```
cccatccctg cccgcagccc cgcgcgccgg ccgagtcgct gagccgcggc
tgccggacgg gacgggaccg gctaggctgg gcgcgcgccc ccgggccccg
ccgtgggcat gggcgcactg ccccgggcgc tgctgctgcc tctgctggcc
cagtggctcc tgcgcgccgc cccggagctg gcccccgcgc ccttcacgct
gccccteegg gtggecgcgg ccacgaaccg cgtagttgcg cccaccccgg
gacccgggac ccctgccgag cgccacgccg acggcttggc gctcgccctg
gagcctgccc tggcgtcccc cgcgggcgcc gccaacttct tggccatggt
agacaacctg caggggact ctggccgcgg ctactacctg gagatgctga
tcgggacccc cccgcagaag ctacagattc tcgttgacac tggaagcagt
aactttgccg tggcaggaac cccgcactcc tacatagaca cgtactttga
cacagagagg tctagcacat accgctccaa gggctttgac gtcacagtga
agtacacaca aggaagctgg acgggcttcg ttggggaaga cctcgtcacc
atccccaaag gcttcaatac ttctttttctt gtcaacattg ccactatttt
tgaatcagag aatttctttt tgcctgggat taaatggaat ggaatacttg
gcctagctta tgccacactt gccaagccat caagttctct ggagaccttc
ttcgactccc tggtgacaca agcaaacatc cccaacgttt tctccatgca
gatgtgtgga gccggcttgc ccgttgctgg atctgggacc aacggaggta
gtcttgtctt gggtggaatt gaaccaagtt tgtataaagg agacatctgg
tataccccta ttaaggaaga gtggtactac cagatagaaa ttctgaaatt
ggaaattgga ggccaaagcc ttaatctgga ctgcagagag tataacgcag
acaaggccat cgtggacagt ggcaccacgc tgctgcgcct gccccagaag
gtgtttgatg cggtggtgga agctgtggcc cgcgcatctc tgattccaga
attctctgat ggtttctgga ctgggtccca gctggcgtgc tggacgaatt
cggaaacacc ttggtcttac ttccctaaaa tctccatcta cctgagagac
gagaactcca gcaggtcatt ccgtatcaca atcctgcctc agctttacat
tcagcccatg atgggggccg gcctgaatta tgaatgttac cgattcggca
tttccccatc cacaaatgcg ctggtgatcg gtgccacggt gatggagggc
ttctacgtca tcttcgacag agcccagaag agggtgggct cgcagcgag
cccctgtgca gaaattgcag gtgctgcagt gtctgaaatt tccgggcctt
tctcaacaga ggatgtagcc agcaactgtg tccccgctca gtctttgagc
gagcccattt tgtggattgt gtcctatgcg ctcatgagcg tctgtggagc
catcctcctt gtcttaatcg tcctgctgct gctgccgttc cggtgtcagc
gtcgccccg tgaccctgag gtcgtcaatg atgagtcctc tctggtcaga
catcgctgga aatgaatagc caggcctgac ctcaagcaac catgaactca
gctattaaga aaatcacatt tccagggcag cagccgggat cgatggtggc
gctttctcct gtgcccaccc gtcttcaatc tctgttctgc tcccagatgc
cttctagatt cactgtcttt tgattcttga ttttcaagct ttcaaatcct
ccctacttcc aag
```

Figure 8

```
MGALARALLLPLLAQWLLRAAPELAPAPFTLPLRVAAATNRVVAPTPGPGTPAERHAD
GLALALEPALASPAGAANFLAMVDNLQGDSGRGYYLEMLIGTPPQKLQILVDTGSSNF
AVAGTPHSYIDTYFDTERSSTYRSKGFDVTVKYTQGSWTGFVGEDLVTIPKGFNTSFL
VNIATIFESENFFLPGIKWNGILGLAYATLAKPSSSLETFFDSLVTQANIPNVFSMQM
GAGLPVAGSGTNGGSLVLGGIEPSLYKGDIWYTPIKEEWYYQIEILKLEIGGQSLNL
DCREYNADKAIVDSGTTLLRLPQKVFDAVVEAVARASLIPEFSDGFWTGSQLACWTNS
ETPWSYFPKISIYLRDENSSRSFRITILPQLYIQPMMGAGLNYECYRFGISPSTNALV
IGATVMEGFYVIFDRAQKRVGFAASPCAEIAGAAVSEISGPFSTEDVASNCVPAQSLS
EPILWIVSYALMSVCGAILLVLIVLLLLPFRCQRRPRDPEVVNDESSLVRHRWK
```

MODULATION OF Aβ LEVELS BY β-SECRETASE BACE2

This application claims priority under 35 U.S.C. §119(e) to U.S. Provisional Application No. 60/215,729 filed Jun. 28, 2000.

BACKGROUND OF THE INVENTION

1. Field of the Invention

The present invention concerns methods and means for the identification and use of modulators of β-amyloid (Aβ) levels obtained by the proteolytic processing of the β-amyloid precursor protein, APP.

2. Description of the Related Art

A number of important neurological diseases, including Alzheimer's disease (AD), cerebral amyloid angiopathy (CAA), and prion-mediated diseases are characterized by the deposition of aggregated proteins, referred to amyloid, in the central nervous system (CNS) (for reviews, see Glenner et al., *J. Neurol. Sci.* 94:1–28 [1989]; Haan et al., *Clin. Neurol. Neurosurg.* 92(4):305–310 [1990]). These highly insoluble aggregates are composed of nonbranching, fibrillar proteins with the common characteristic of β-pleated sheet conformation. In the CNS, amyloid can be present in cerebral and meningeal blood vessels (cerebrovascular deposits) and in the brain parenchyma (plaques). Neuropathological studies in human and animal models indicate that cells proximal to amyloid deposits are disturbed in their normal functions (Mandybur, *Acta Neuropathol.* 78:329–331 [1989]; Kawai et al., *Brain Res.* 623:142–146 [1993]; Martin et al., *Am. J. Pathol.* 145:1348–1381 [1994]; Kalaria et al., *Neuroreport* 6:477–480 [1995]; Masliah et al., *J. Neurosci.* 16:5795–5811 [1996]; Selkoe, *J. Biol. Chem.* 271:18295–18298 [1996]; Hardy, *Trends Neurosci* 20:154–159 [1997]).

AD and CAA share biochemical and neuropathological markers, but differ somewhat in the extent and location of amyloid deposits as well as in the symptoms exhibited by affected individuals. The neurodegenerative process of AD, the most common neurodegenerative disorder worldwide, is characterized by the progressive and irreversible deafferentation of the limbic system, association neocortex, and basal forebrain accompanied by neuritic plaque and tangle formation (for a review, see Terry et al., "Structural alteration in Alzheimer's disease," In: Alzheimer's disease, Terry et al. Eds., 1994, pp. 179–196, Raven Press, New York). Dystrophic neurites, as well as reactive astocytes and microglia, are associated with these amyloid-associated neuritic plaques. Although the neuritic population in any given plaque is mixed, the plaques generally are composed of spherical neurites that contain synaptic proteins, APP (type I), and fusiform neurites containing cytoskeletal proteins and paired helical filaments (PHF; type II).

CAA patients display various vascular syndromes, of which the most documented is cerebral parenchymal hemorrhage. Cerebral parenchymal hemorrhage is the result of extensive amyloid deposition within cerebral vessels (Hardy, *Trends Neurosci* 20:154–159 [1997]; Haan et al., *Clin. Neurol. Neurosurg.* 92:305–310 [1990]; Terry et al., [1994] supra; Vinters, *Stroke* 18:211–224 [1987]; Itoh et al., *J. Neurosurgical Sci.* 116:135–141 [1993]; Yamada et al., *J. Neurol. Neruosurg. Psychiatry* 56:543–547 [1993]; Greenberg et al., *Neurology* 43:2073–2079 [1993]; Levy et al., *Science* 248:1124–1126 [1990]). In some familial CAA cases, dementia was noted before the onset of hemorrhages, suggesting the possibility that cerebrovascular amyloid deposits may also interfere with cognitive functions.

Both AD and CAA are characterized by the accumulation of senile plaques in the brains of the affected individuals. The main amyloid components is the amyloid β protein (Aβ), also referred to as amyloid β or β-amyloid peptide, derived from proteolytic processing of the β-amyloid precursor protein, β-APP or simply APP. For review in connection with AD see, Selkoe, D. J. *Nature* 399: A23–A31 (1999). Aβ is produced by proteolytic cleavage of an integral membrane protein, termed the β-amyloid precursor protein (βAPP).

The Aβ peptide, which is generated from APP by two putative secretases, is present at low levels in the normal CNS and blood. Two major variants, $A\beta_{1-40}$ and $A\beta_{1-42}$ are produced by alternative carboxy-terminal truncation of APP (Selkoe et al. [1988] *Proc. Natl. Acad. Sci. USA* 85:7341–7345; Selkoe [1993] *Trends Neurosci* 16:403–409). $A\beta_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy [1997], supra; Haan et al. [1990], supra; Terry et al., [1994] supra; Vinters [1987], supra; Itoh, et al. [1993], supra; Yamada et al. [1993], supra; Greenberg et al. [1993], supra; Levy et al. [1990], supra). These vascular lesions are the hallmark of CAA, which can exist in the absence of AD.

The precise mechanisms by which neuritic plaques are formed and the relationship of plaque formation to the AD-associated, and CAA-associated neurodegenerative processes are not well defined. However, evidence indicates that dysregulated expression and/or processing of APP gene products or derivatives of these gene products are involved in the pathophysiological process leading to neurodegeneration and plaque formation. For example, missense mutations in APP are tightly linked to autosomal dominant forms of AD (Hardy [1994] *Clin. Geriatr. Med.* 10:239–247; Mann et al. [1992] *Neurodegeneration* 1:201–215). The role of APP in neurodegenerative diseases is further implicated by the observation that persons with Down's syndrome who carry an additional copy of the human APP (HAPP) gene on their third chromosome 21 show an overexpression of hAPP (Goodison et al. [1993] *J. Neuropathol. Exp. Neurol.* 52:192–198; Oyama, et al. [1994] *J. Neurochem,* 62:1062–1066) as well as a prominent tendency to develop AD-type pathology early in life (Wisniewski et al. [1985] *Ann. Neurol.* 17:278–282). Mutations in Aβ are linked to CAA associated with hereditary cerebral hemorrhage with amyloidosis (Dutch HCHWA) (Levy, et al. [1990], supra), in which amyloid deposits preferentially occur in the cerebrovascular wall with some occurrence of diffuse plaques (Maat-Schieman et al. [1994] *Acta Neuropathol* 88:371–8; Wartendorff et al. [1995] *J. Neurol. Neurosurg. Psychiatry* 58:699–705). A number of HAPP point mutations that are tightly associated with the development of familial AD encode amino acid changes close to either side of the Aβ peptide (for a review, see, e.g., Lannfelt et al. [1994] *Biochem. Soc. Trans.* 22:176–179; Clark et al. [1993]*Arch. Neurol.* 50:1164–1172). Finally, in vitro studies indicate that aggregated Aβ can induce neurodegeneration (see, e.g., Pike et al. (1995) *J. Neurochem.* 64:253–265).

APP is a glycosylated, single-membrane-spanning protein expressed in a wide variety of cells in many mammalian tissues. Examples of specific isotypes of APP which are currently known to exist in humans are the 695-amino acid polypeptide (APP695) described by Kang et al. (1987) *Nature* 325:733–736, which is designated as the "normal" APP. A 751-amino acid polypeptide (APP751) has been described by Ponte et al. (1988) *Nature* 331:525–527 and Tanzi et al. (1988) *Nature* 331:528–530. A 770-amino acid isotype of APP (APP770) is described in Kitaguchi et al. (1988) *Nature* 331:530–532. A number of specific variants of APP have also been described having mutations which can differ in both position and phenotype. A general review of such mutations is pivoted in Hardy (1992) *Nature Genet.* 1:233–235. A mutation of particular interest is designated the "Swedish" mutation where the normal Lys-Met residues at positions 595 and 596 are replaced by Asn-Leu. This mutation is located directly upstream of the normal P-secretase cleavage site of APP, which occurs between residues 596 and 597 of the 695 isotype.

APP is post-translationally processed by several proteolytic pathways resulting in the secretion of various fragments or intracellular fragmentation and degradation. F. Checler, *J. Neurochem.* 65:1431–1444 (1995). The combined activity of β-secretase and γ-secretase on APP releases an intact Aβ-amyloid peptide (Aβ), which is a major constituent of amyloid plaques. Initial cleavage of APP by β-secretase generates soluble APPβ and membrane-associated β-CTF that can be further processed by γ-secretase to generate a 40 or a 42 amino acid peptide (Aβ40 or Aβ42). Alternatively, APP processing by α-secretase leads to the formation of soluble APPα and membrane associated α-CTF the latter being a substrate for γ-secretase to generate the non-amyloidogenic p3. Aβ is an approximately 43 amino acid peptide, which comprises residues 597–640 of the 695 amino acid isotype of APP. Internal cleavage of Aβ by a α-secretase inhibits the release of the full-length Aβ peptide. Although the extent of pathogenic involvement of the secretases in AD progression is not fully elucidated, these proteolytic events are known to either promote or inhibit Aβ formation, and thus are thought to be good therapeutic candidates for AD.

The polytopic transmembrane protein presenilin has been strongly implicated in γ-secretase activity (for review see Haass and De Strooper, *Science* 286: 916–919 [1999]). Mutagenesis of two transmembrane aspartates of presenilin led to the inactivation of γ-secretase activity in cellular assays (Wolfe et al., *Nature* 398: 513–517 [1999]). As a result, both α- and β-CTFs accumulated and Aβ formation was significantly decreased. Similar effects were seen upon inhibition of γ-secretase using substrate analogs (Wolfe et al., *J. Med. Chem.* 41: 6–9 [1998]). While it remains to be determined whether presenilin is sufficient as γ-secretase or whether it requires another unique co-factor of so far unknown nature to exert its function Presenilin 1 and γ-secretase activity have recently been shown to co-precipitate from membrane extracts (Li et al. *Proc. Natl. Acad Sci. USA* 97(11):6138–43 [2000]).

As discussed above, there are at least two proteases involved in the generation of Aβ, referred to as β- and γ-secretases (Citron et al., *Neuron* 17:171–179 [1996]; Seubert et al., *Nature* 361:260–263 [1993]; Cai et al., *Science* 259:514–516 [1993]; and Citron et al., *Neuron* 14:661–670 [1995]). There have been intense efforts in recent years to identify and characterize these enzymes. Recently five independent groups have reported cloning and characterization of genes corresponding to a β-secretase (Vassar et al., *Science* 286: 735–741 [1999]; Yan et al., *Nature* 402: 533–537 [1999]; Sinha et al., *Nature* 402: 537–540 [1999]; Hussain et al., *Mol. Cell. Neurosci.* 14: 419–427 [1999]; Lin et al. *Proc. Natl. Acad. Sci. USA* 97: 1456–1460 [2000]). The membrane-bound aspartyl protease has been variously referred to as β-site APP-cleaving enzyme (BACE), Aspartyl protease-2 (Asp2), memapsin 2 or simply as β-secretase. However, the deduced amino acid sequence of the polypeptide chain reported by all five groups is identical. The cloned enzyme possesses many of the characteristics expected of an authentic β-secretase. In particular, BACE overexpression resulted in an increase in both β-NTF and Aβ levels while suppression of BACE with antisense oligonucleotides led to a significant reduction of these cleavage products. As predicted for the genuine β-secretase, the Swedish double mutant of APP (APPsw, Mullan et al., *Nature Genetics* 1: 345–347 [1992]; Citron et al, *Nature* 360: 672–674 [1992]; Cai et al., *Science* 259: 514–516 [1993]) was cleaved more efficiently by BACE. Taken together, these results have led to the notion that BACE is the main β-secretase activity.

A close homolog of BACE, designated DRAP or BACE2, has been described recently (Acquati et al., FEBS Lett. 468: 59–64 [2000], GenBank accession numbers for the human and mouse cDNA sequences: AF050171 and AF051150, respectively; Bennett et al., *J. Biol. Chem.* 275:37712–7 [2000]). BACE and BACE2 share 64% amino acid similarity but the role of BACE2 in APP processing has not yet been elucidated. Strikingly, BACE2 expression in brain appears to be very low and this observation has contributed to the assumption that BACE2's role in β-secretase cleavage might only be minor (Bennett et al., ibid).

SUMMARY OF THE INVENTION

Experimental data disclosed herein confirm that BACE2 indeed possesses β-secretase activity when reconstituting β-secretase cleavage in a cell-free assay using wild-type (wt) or Swedish mutant forms of APP751 as a substrate. However, this activity is weaker than the β-secretase activity of BACE. The invention is further based on the unexpected finding that while BACE2 overexpression in HEK293 cells had a moderate effect on β-NTF formation, it strikingly suppressed Aβ production in either the presence or absence of additional exogenous copies of BACE. BACE2 also modulated Aβ levels in neuronal SKN cells and thus its effect was not restricted to non-neuronal HEK293 cells. The suppression of Aβ production by BACE2 did not appear to require its ability to cleave at the β-secretase site. Aβ levels were similarly suppressed in cells carrying a C-terminal 100 amino acids fragment of amyloid precursor protein (APP) truncated to mimic β-secretase cleavage. It is suggested that BACE2 functions as a modulator of Aβ production by promoting the alternative non-amyloidogenic APP processing pathway such as that mediated by α-secretase activity.

In one aspect, the invention concerns a method of modulating the enzymatic production of Aβ-amyloid peptide (Aβ) from β-amyloid precursor protein (APP) or a fragment thereof by contacting said APP or APP fragment with a BACE2 polypeptide or an agonist or antagonist thereof. In a specific embodiment, the method concerns the inhibition of Aβ production from APP or an APP fragment by using BACE2 or an agonist of BACE2.

In another aspect, the invention concerns a method of inhibiting the formation of an Aβ-amyloid peptide (Aβ) from Aβ-amyloid precursor protein (APP) or a fragment thereof by contacting APP of an APP fragment with a BACE2 polypeptide or an agonist thereof.

In yet another aspect, the invention concerns a method of inhibiting the release of a full-length β-amyloid (Aβ) polypeptide from β-amyloid precursor protein (APP) or a fragment thereof, comprising cleaving said APP or APP fragment by a BACE2 polypeptide or an agonist thereof at a site interfering with '-secretase processing of the APP or APP fragment.

In all aspects, APP may, for example, be a native sequence human APP including the 695-amino acid isotype and the isotype containing the so called Swedish mutation. The APP fragment specifically includes, without limitation, β-CTF. The methods may be performed in the presence of an α-secretase activity and/or a γ-secretase activity and/or a β-secretase activity other than BACE2. The additional β-secretase activity may, for example, be due to the presence of an enzyme having a pH optimum at about pH 6.5–7.0, and an estimated molecular weight of about 32–39 kDa as calculated from radiation inactivation analysis of HEK293 cell membrane extracts, or about 20–26 kDa as calculated from radiation inactivation analysis of human brain samples, with a candidate compound. Alternatively or in addition, the additional β-secretase activity may be due to the presence of a β-secretase enzyme having a pH optimum at about pH 4.5–5.0 and an estimated molecular weight of about 50–60 kDa as calculated from radiation inactivation analysis of HEK293 cell membrane extracts or human brain samples (BACE1). These β-secretase activities are further disclosed and characterized in co-pending application Ser. No. 09/566, 746 filed on May 9, 2000 for Novel β-Secretase and Modulation of β-Secretase Activity the entire disclosure of which is hereby expressly incorporated by reference.

In a further aspect, the invention concerns a method for identifying a modulator of the enzymatic production of β-amyloid peptide (Aβ) from β-amyloid precursor protein (APP) or a fragment thereof, comprising contacting APP or an APP fragment and BACE2 with a candidate compound and monitoring the effect of the candidate compound on the production of Aβ. In a preferred embodiment, the method is used to identify inhibitors of the enzymatic production of Aβ from APP or a fragment thereof. The effect of the candidate compound on the production of Aβ may, for example, be monitored by measuring the amount of Aβ formed but other method of monitoring are also within the scope of the invention. In a preferred embodiment, the method is used to identify inhibitors that reduce the amount of Aβ formed by at least about 50%, preferably by at least about 75%, more preferably by at least about 85%, most preferably by at least about 90%.

Just as in the previous aspects, APP may, for example, be a native sequence human APP including the 695-amino acid isotype and the isotype containing the so called Swedish mutation. The APP fragment specifically includes, without limitation, β-CTF . The method may be performed in the presence of an α-secretase activity and/or a γ-secretase activity and/or a β-secretase activity other than BACE2. The additional β-secretase activity may, for example, be due to the presence of an enzyme having a pH optimum at about pH 6.5–7.0, and an estimated molecular weight of about 32–39 kDa as calculated from radiation inactivation analysis of HEK293 cell membrane extracts, or about 20–26 kDa as calculated from radiation inactivation analysis of human brain samples, with a candidate compound. Alternatively or in addition, the additional β-secretase activity may be due to the presence of a β-secretase enzyme having a pH optimum at about pH 4.5–5.0 and an estimated molecular weight of about 50–60 kDa as calculated from radiation inactivation analysis of HEK293 cell membrane extracts or human brain samples (BACE1).

In a still further aspect, the invention concerns a modulator of the enzymatic production of Aβ-amyloid peptide (Aβ) from Aβ-amyloid precursor protein (APP) or a fragment thereof, identified by the foregoing method. The modulator preferably is an inhibitor, and may, for example, be a polypeptide, peptide, or small molecule.

In an additional aspect, the invention concerns a method for reducing the amount of Aβ-amyloid deposits in the central nervous system (CNS) of a mammal comprising administering to the mammal an effective amount of BACE2 or an agonist thereof.

In another aspect, the invention concerns a method for the treatment of Alzheimer's disease (AD), an AD-type pathology or cerebral amyloid angiopathy in a mammalian patient, comprising administering to the patient an effective amount of BACE2 or an agonist thereof.

BRIEF DESCRIPTION OF THE DRAWINGS

FIG. 7 shows the nucleotide sequence of human BACE2 (SEQ ID NO: 1).

FIG. 8 shows the deduced amino acid sequence of human BACE2 (SEQ ID NO: 2).

DETAILED DESCRIPTION OF THE PREFERRED EMBODIMENT

Figure 1:
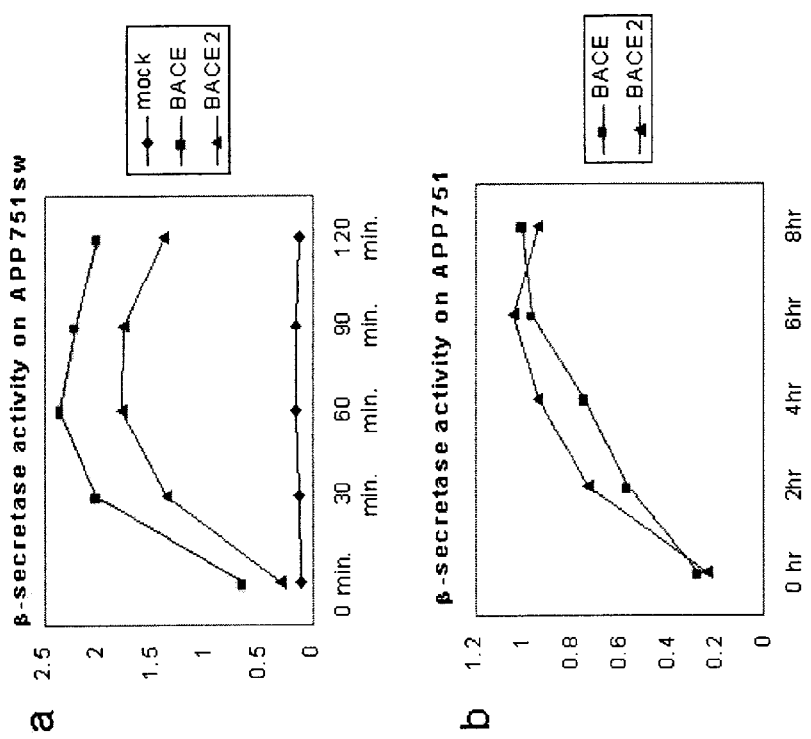
FIG. 1. BACE2 possesses β-secretase activity in vitro. β-secretase cleavage was reconstituted at pH 4.5 using extracts derived from BACE and BACE2 as well as mock-transfected HEK293T cells. The kinetics of β-NTF formation using partially purified native APP751sw (a) and APP751 (b) as a substrate are shown.

A wide variety of proteins may be involved in the processing or regulation of processing of βAPP in order to generate β-Amyloid (Aβ) peptide, the aggregation and extracellular deposition of which in the brain is a hallmark of Alzheimer's disease pathology. Therefore, any therapeutic strategy evolved to prevent, delay, slow down or halt the deposition of these plaques in Alzheimer's patients should take into account not only the activities of various secretases, but also various proteins involved the regulation or modulation of such enzymes. A novel activity of BACE2 as disclosed herein provides yet another target for screening of compounds to identify potential drug candidates for the treatment (including prevention) of Alzheimer's disease and other neurodegenerative disorders. The present invention provides a way for screening of agonists or activators of BACE2-mediated suppression of Aβ peptide, and for the identification of potential drugs for Alzheimer's disease.

I. DEFINITIONS

Before the present invention is described, it is to be understood that this invention is not limited to particular methodology described. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention pertains. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, "β-amyloid precursor protein" (APP or βAPP) refers to a polypeptide that is encoded by a gene of the same name localized in humans on the long arm of chromosome 21 and that includes a β-amyloid protein region within its carboxy terminal region.

The term "BACE2" is used herein to refer to native sequence BACE2 from any animal, e.g. mammalian, species, including humans, and BACE2 variants (which are further defined below). The BACE2 polypeptides may be isolated from a variety of sources, including human tissue types or prepared by recombinant and/or synthetic methods.

"Native sequence BACE2" refers to a polypeptide having the same amino acid sequence as a BACE2 polypeptide occurring in nature regardless of its mode of preparation. A native sequence BACE2 may be isolated from nature, or prepared by recombinant and/or synthetic methods. The term "native sequence BACE2" specifically encompasses naturally occurring truncated or secreted forms, naturally occurring variant forms (e.g. alternatively spliced forms), and naturally occurring allelic variants of BACE2, whether known or to be discovered in the future.

The term "BACE2 variant" refers to amino acid sequence variants of a native sequence BACE2, containing one or more amino acid substitution and/or deletion and/or insertion in the native sequence. The amino acid sequence variants generally have at least about 75%, preferably at least about 80%, more preferably at least about 85%, even more preferably at least about 90%, most preferably at least about 95% sequence identity with the amino acid sequence of a native sequence BACE2.

"Sequence identity" is defined as the percentage of amino acid residues in a candidate sequence that are identical with the amino acid residues in a native sequence polypeptide after aligning the sequences and introducing gaps, if necessary, to achieve the maximum percent sequence identity, and not considering any conservative substitutions as part of sequence identity. The % sequence identity values are generated by NCBI BLAST2.0 software as defined by Altschul et al. (1997), *Nucleic Acids Res.* 25:3389–3402. In a preferred embodiment, an amino acid sequence variant of a native sequence BACE2 is encoded by nucleic acid hybridizing under stringent conditions to the complement of the nucleic acid shown in FIG. 7 (SEQ ID NO: 1), and retains a biological activity of a native sequence BACE2.

"Stringent" hybridization conditions are sequence dependent and will be different with different environmental parameters (e.g., salt concentrations, and presence of organics). Generally, stringent conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a complementary nucleic acid. The $T_m$ is the temperature (under defined ionic strength and pH) at which 50% of a nucleic acid (e.g., tag nucleic acid) hybridizes to a perfectly matched probe "Stringent" wash conditions are ordinarily determined empirically for hybridization of each set of tags to a corresponding probe array. The arrays are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is more important than the measure of any single parameter. See, e.g., Wetmur et al., *J. Mol. Biol.* 31:349–70 (1966), and Wetmur, *Critical Reviews in Biochemistry and Molecular Biology*,26(34):227–59 (1991). In a preferred embodiment, "stringent conditions" or "high stringency conditions," as defined herein, may be hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The term "recombinant" when used with reference to a cell, animal, or virus indicates that the cell, animal, or virus encodes a foreign DNA or RNA. For example, recombinant cells optionally express nucleic acids (e.g., RNA) not found within the native (non-recombinant) form of the cell.

"Mammal" for purposes of the present inventin refers to any animal classified as a mammal, including humans, domestic and farm animals, and zoo, sports, or pet animals, such as dogs, horses, cats, cows, etc. Preferably, the mammal herein is human.

The term "biological activity" in connection with BACE2 is used to refer to the ability of a BACE2 molecule (including variants of native sequence BACE2) to modulate, preferably suppress the enzymatic production of β-amyloid peptide (Aβ) from the β-amyloid precursor protein (APP) or a fragment thereof, irrespective of the mechanism by which the modulation (suppression) occurs. In a preferred embodiment, the BACE2 "biological activity" is the ability to inhibit β-amyloid formation from native sequence APP or a fragment thereof, including fragment(s) obtained by β-secretase processing, e.g. β-CTF (CT100). In another preferred embodiment, BACE 2 "biological activity" is the ability to cleave APP or a fragment thereof (including, but not limited to β-CTF) such that the release of a full-length Aβ peptide by further enzymatic processing is inhibited.

The term "BACE2 agonist" or "agonist of BACE2 (biological) activity" is used in the broadest sense and refers to a molecule that stimulates the production of a native sequence BACE2, enhances a biological activity of a native sequence BACE2 and/or mimics a biological activity of a native sequence BACE2. Thus, a BACE2 agonist may specifically change the function and/or expression of a native sequence BACE2 polypeptide, or the efficiency of signaling through a pathway involving a native sequence BACE2 polypeptide.

Similarly, the term "BACE2 antagonist" or "antagonist of BACE2 activity" is used in the broadest sense and includes any molecule that partially or fully blocks, inhibits or neutralizes a biological activity of a native sequence BACE2 polypeptide.

The terms "Aβ-amyloid protein", "amyloid β protein", "β-amyloid peptide", "amyloid β peptide" and "Aβ", which are used interchangeably, refer to all β-amyloid peptides or polypeptides generated by N-terminal proteolysis of APP followed by carboxy-terminal truncation, including any peptide or polypeptide containing from about 38 to about 44 amino acids, inclusive, and preferably comprising residues 597–640 of the 695 amino acid isotype human APP, including, without limitation, the two major variants, $A\beta_{1-40}$ and $A\beta_{1-42}$, as well as corresponding regions of other isotypes of human APP and non-human mammalian homologues of APP. After this disclosure others will, perhaps, discover other Aβ-amyloid proteins, all of which are all intended to come within the scope of the present invention.

The term p3 peptide refers to the approximately 26 amino acid segment resulting from α-secretase activity, generally occurring between residues 612 and 613 of the 695 APP isoform and the heterogeneous γ-secretase cleavge of APP in the region of residue 638 to 640 of the 695 amino acid isotype human APP.

The terms "APP secretase," "secretase" and "secretase activity" as used interchangeably herein refer to any proteolytic enzyme and/or activity which results in the secretion of various fragments or intracellular fragmentation and degradation of APP. This includes α-secretase, β-secretase, γ-secretase, and any similar but as of yet unidentified enzymes, which cause the proteolysis of either APP or Aβ.

The terms "β-secretase " and "β-secretase activity" as used interchangeably herein refer to the enzyme or enzymes responsible for proteolysis of APP at the N-terminal cleavage site of APP, which occurs between residues 596 and 597 of the 695 isotype of APP (Kang et al. (1987) *Nature* 325:733–736) and between residues 652 and 653 of the 751 isotype of APP (Ponte et al. (1988) *Nature* 331:525–527). A secondary cleavage by β-secretase occurs between residues 605 and 606 of the 695 APP isoform and between residues 661 and 662 of the 751 APP isoform (Higaki et al. (1996) *Neuron* 14:651–659). The terms are used in the broadest sense and include isolated, partially or fully purified, recombinantly produced enzymes, cells or cell preparations (including membrane preparations) comprising a β-secretase enzyme, and any solution or mixture comprising a β-secretase enzyme.

The term "APP/β-secretase mixture" as used herein refers to the isolated APP and β-secretase as a complex and/or as a mixture of the two substances.

The term "α-secretase" and "α-secretase activity" are used interchangeably, and refer to the enzyme or enzymes capable of producing a cleavage within the β-amyloid domain of APP or the C-terminal fragment of APP resulting from β-secretase processing. The processing by α-secretase activity, generally occurs between residues 612 and 613 of the 695 APP isoform or between residues 16 and 17 of the C-terminal fragment of APP resulting from β-secretase processing. The terms are used in the broadest sense and include isolated, partially or fully purified, recombinantly produced enzymes, cells or cell preparations (including membrane preparations) comprising an α-secretase enzyme, and any solution or mixture comprising a α-secretase enzyme.

The terms "γ-secretase " and "γ-secretase activity" are used interchangeably, and refer to the enzyme or enzymes responsible for generating the C-termini of the β-amyloid peptides and p3 peptide by cleaving within the transmembrane region of APP. The terms are used in the broadest sense and include isolated, partially or fully purified, recombinantly produced enzymes, cells or cell preparations (including membrane preparations) comprising an γ-secretase enzyme, and any solution or mixture comprising a γ-secretase enzyme.

The term "Alzheimer's disease" (abbreviated herein as "AD") as used herein refers to a condition associated with formation of neuritic plaques comprising β-amyloid protein primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing β-amyloid protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

The term "cerebral amyloid angiopathy" (abbreviated herein as CAA) as used herein refers to a condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh, et al. (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral amyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "Aβ-amyloid deposit" as used herein refers to a deposit in the brain composed of Aβ as well as other substances.

The term "non-amyloidogenic" refers to a process which reduces or eliminates the production of Aβ-amyloid.

By "antibody" is meant an immunoglobulin protein which is capable of binding an antigen. Antibody as used herein is meant to include the entire antibody as well as any antibody fragments (e.g., F(Ab')$_2$, Fab', Fab, Fv) capable of binding the epitope, antigen or antigenic fragment of interest.

Antibodies of the invention are immunoreactive or immunospecific for and therefore specifically and selectively bind specific proteolytic products of the APP protein. Antibodies for each proteolytic product are preferably immunospecific—i.e., not substantially cross-reactive with other proteolytic products of APP. The term "antibody" encompasses all types of antibodies both polyclonal and monoclonal antibodies, and produced using a suitable, e.g. peptide antigen.

By "purified antibody" is meant one which is sufficiently free of other proteins, carbohydrates, and lipids with which it is naturally associated. Such an antibody "preferentially binds" to a proteolytic APP protein product (or an antigenic fragment thereof), i.e., does not substantially recognize and bind to other antigenically-unrelated molecules. A purified antibody of the invention is preferably immunoreactive with and immunospecific for a particular APP protein product (e.g., βNTF) and more preferably will not react with other APP protein products.

By "antigenic fragment" of an APP proteolytic product is meant a portion of such a protein which is capable of binding an antibody used in the assay of the invention.

By "binds specifically" is meant high avidity and/or high affinity binding of an antibody to a specific polypeptide, i.e., epitope of a APP protein product. Antibody binding to its epitope on this specific polypeptide is preferably stronger than binding of the same antibody to any other epitope, particularly those which may be present in molecules in association with, or in the same sample, as the specific polypeptide of interest, e.g., binds more strongly to APP protein product than other epitopes so that by adjusting binding conditions the antibody binds almost exclusively to the APP protein product. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound on polypeptide of interest, e.g., by use of appropriate controls. In general, antibodies of the invention bind to a particular APP protein product with a binding affinity of $10^7$ moles/liter or more, preferably $10^8$ mole/liters or more. In general, an antibody with a binding affinity of $10^6$ moles/liter or less is not useful in that it will not bind antigen at a detectable level using conventional methodology currently used.

By "detectably labeled antibody" or "detectably labeled anti-βNTF" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.).

The term "compound" as used herein describes any molecule, e.g., protein, naturally occurring substances, synthesized protein or small molecule pharmaceutical, with the capability of affecting secretase activity. Such compounds may be used to treat the molecular and clinical phenomena associated with amyloid-associated disorders, and specifically AD, CAA and prion-medicated disorder.

The terms "effective dose", "effective amount" and "amount effective" are used interchangeably, and refer to an administration of a compound sufficient to provide the desired physiological and/or psychological change. This will vary depending on the patient, the disease and the treatment. The dose may either be a therapeutic dose, in which case it should sufficiently alter levels of amyloid plaques in the subject to alleviate or ameliorate the symptoms of the disorder or condition, or a prophylactic dose, which should be sufficient to prevent accumulation of amyloid plaques to an undesirable level. The terms "treatment," "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease. The therapeutic agents that can be identified using the assay of the invention are particularly useful in the treatment of any disease associated with the deposition of β-amyloid, including AD, hereditary cerebral hemorrhage with amyloidosis, and prion-mediated disorders, and the like.

The terms "modulate", "alter" and grammatical variants thereof, when used in connection with the methods of the present invention, include any and all modifications, such as inhibition or enhancement of β-secretase activity.

II. DESCRIPTION OF PREFERRED EMBODIMENTS

1. Inhibition of β-amyloid production by BACE2 or stimulators of BACE2 activity.

In one aspect, the invention concerns a method for inhibiting Aβ-amyloid formation from APP or the β-secretase product or products of APP by treating APP with an effective amount of BACE2 or a stimulator of BACE2 activity. In this method BACE2 can be any native BACE2 polypeptide, including all isoforms and allelic variants of native human and non-human mammalian BACE2 polypeptides, known or hereinafter identified, as well as any biologically active variant thereof as hereinabove defined. The treatment may be performed in vitro or in vivo. Stimulators of BACE2 activity may be identified as described hereinbelow.

When the treatment is performed in vivo, its objective is the treatment (including prevention) of a neurological disease characterized by the deposition of β-amyloid in the central nervous system. Such diseases include, without limitation, Alzheimer's disease (AD) and AD-type pathologies, including, but not limited to, pathologies associates with Down's syndome, as well as cerebral amyloid angiopathy, whether associated with or existing in the absence of Alzheimer's disease.

In general, BACE2 or a compound identified in an assay described hereinbelow, will reduce the level of β-amyloid plaque in the brain tissue of a mammalian host, including humans. In general, the compounds enhancing the ability of BACE2 to promote non-amyloidogenic cleavage of APP will reduce the level of Aβ-amyloid plaque in brain tissue by enhancing in vivo levels of BACE2-mediated suppression of Aβ production. Therapeutic effects may be seen, for example, by compounds that increase the expression level of BACE2 protein or enhance or activate BACE2-mediated non-amyloidogenic α-secretase-like processing of APP or fragments of APP, resulting in reduced Aβ production. Prophylactic use is also contemplated for individuals at risk of developing Alzheimer's disease (AD), AD-type pathologies and/or cerebral amyloid angiopathy, such as the elderly and/or individuals carrying known mutations linked to AD.

In the in vivo treatment methods, BACE2 or other compounds of the present invention may be administered to the host using any convenient means capable of resulting in the desired target protein activity modulation. Thus, the compound can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, transdermal patches, suppositories, injections, inhalants and aerosols.

As such, administration of the compounds can be achieved in various ways, including oral, buccal, rectal, parenteral, intraperitoneal, intravaginal, intradermal, transdermal, intratracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules. Examples of additives are conventional additives, such as lactose, mannitol, corn starch or potato starch; binders, such as crystalline cellulose, cellulose derivatives, acacia, corn starch or gelatins; disintegrators, such as corn starch, potato starch or sodium carboxymethylcellulose; lubricants, such as talc or magnesium stearate; and if desired, diluents, buffering agents, moistening agents, preservatives and flavoring agents.

The compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol. If desired, conventional additives such as solubilizers, isotonic agents, suspending agents, emulsifying agents, stabilizers and preservatives may also be added. The concentration of therapeutically active compound in the formulation may vary from about 0.5–100 wt. %.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit (e.g., a teaspoonful, tablespoonful, tablet or suppository) contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The compounds are administered to a host in a physiologically acceptable carrier, at a dosage from 5 mg to 1400 mg, more usually from 100 mg to 1000 mg, preferably 500 mg to 700 mg for a dose of 0.5 to 20 mg/kg weight. The dosage for compounds altering (modulating, e.g. enhancing or inhibiting) BACE2 activity is elected so that the BACE2 activity is altered by 10 to 80%, more preferably 20 to 70% and even more preferably 25–50%.

2. Screening Assays

In another aspect, the present invention provides screening assays for identifying modulators (including stimulators and inhibitors) of the ability of BACE2 to interfere with APP amyloidogenic processing resulting in the modulation (e.g. suppression) of A$\beta$ production. BACE2, APP and processing secretases, any or all of which may be present in isolated, immobilized or cell bound form or in the form of membrane-enzyme mixture, are contacted with a candidate compound, or a plurality of candidate compounds, and those candidates are selected that alter, preferably enhance, BACE2-mediated reduction of A$\beta$ production. While the effect of a candidate compound on BACE2 activity is preferably detected by monitoring its ability to alter (e.g. reduce) the amount of A$\beta$ produced, other read-outs of APP or APP fragments cleavage at the $\alpha$, $\beta$ or $\gamma$-secretase cleavage sites are equally suitable. Both cell-free and cell based assays, including assays performed with cell membrane-enzyme preparations are specifically within the scope of the invention.

Candidate compounds which significantly enhance the expression or the ability of BACE2 to promote APP cleavage at or around the $\alpha$-secretase cleavage site are preferred. Such compounds preferably enhance the expression or the ability of BACE2 to reduce the amount of A$\beta$ produced, or any other read-out indicative of $\alpha$-secretase mediated cleavage of APP, by at least about 25%, preferably at least about 50%, more preferably at least about 75%, most preferably at least about 90%, and often at least about 95%. The compounds identified can be used in the treatment of patients, particularly humans, at risk of developing or diagnosed with AD, AD-type pathologies, cerebral amyloid angiopathy or any other pathology associated with the formation of $\beta$-amyloid deposits (e.g. plaques) in the CNS, such as brain.

In one particular embodiment, the assay involves contacting APP or APP fragments of $\beta$-secretase processing or the C-terminal 100 residues of APP/BACE2 as individual components or as a mixture or complex with a test compound, and thereafter determining the level of soluble product of APP proteolysis, particularly A$\beta$ and/or $\beta$-NTF and/or p3 and/or $\alpha$-CTF. In cell-based assays, including assays using membrane preparations, cell membranes (obtained by cell lysis) may be additionally assayed for cell-associated products of APP proteolysis, i.e. CTFs ($\alpha$-CTF and/or $\beta$-CTF ). The APP and BACE2 which are contacted with the compound can be both isolated from cell membranes obtained from cells expressing both APP and BACE2 or can be isolated from cells expressing either APP or $\beta$-secretase and then combined together. Alternatively, APP and/or BACE2 may be partially or fully synthesized by traditional chemical synthesis and/or recombinant DNA technology.

In a special embodiment, cells engineered to recombinantly express APP or APP fragments of $\beta$-secretase processing or the C-terminal 100 residues of APP and/or BACE2 can be used. For example, following incubation of cells overexpressing BACE2/APP with the test compound, the supernatant is assayed for levels of soluble products of APP proteolysis, i.e., A$\beta$ and/or $\beta$-NTF and/or p3, whereas cell membranes obtained by cell lysis are assayed for cell-associated products of APP proteolysis, i.e. CTFs ($\alpha$-CTF or $\beta$-CTF). Detection of the APP proteolytic products can be accomplished using any of a number of methods to determine the absence or presence or altered amounts of the differentially expressed polypeptide in the test sample. In general, antibodies that specifically bind a differentially expressed polypeptide of the invention are added to a sample, and incubated for a period of time sufficient to allow binding to the epitope, usually at least about 30 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g., fluorescein, rhodamine, Texas Red, etc.). Any suitable alternative method of qualitative or quantitative detection of levels or amounts of differentially expressed polypeptide can be used, for example western blot, immunoprecipitation, radioimmunoassay, etc. In a preferred embodiment, an enzyme-linked immunosorbent assay (ELISA) is used to detect the presence of the APP proteolytic products, A$\beta$, p3, $\beta$-NTF and CTFs. Quantitation of multiple samples can be made more time efficient by running the assay in an ELISA format for rapid quantitation by spectrophotometric or colorimetric detection.

Cells overexpressing BACE2/APP or APP fragments of $\beta$-secretase processing or the C-terminal 100 residues of APP can be grown in 96-well tissue culture plates, exposed to various potential compounds at different concentrations and/or for different time, and an aliquot of culture supernatant taken for estimation of APP proteolytic products released from cells, i.e. A$\beta$, p3,and/or $\beta$-NTF, by ELISA. Cell-associated APP proteolytic products (CTFs, i.e. $\alpha$-CTF or $\beta$-CTF) can be conveniently estimated by washing cells, lysing cells with mild detergent, washing away all the cytosolic contents, and estimating the amount of membrane-bound CTFs by carrying out ELISA in the same plate. If the compound reduces the level of A$\beta$ and increases the level of CTFs ($\alpha$-CTF and/or $\beta$-CTF) products, e.g., as compared with a previously known standard then the compound is a candidate for the treatment of patients with amyloid-associated disorders.

In a preferred embodiment, the present invention provides an assay methodology for identifying compounds which have an effect on (preferably enhance) BACE2-mediated suppression of A$\beta$ by promoting $\alpha$-secretase-like cleavage, using membrane-enzyme mixtures. In assays using cell-membranes, background levels of APP proteolytic products may be removed before the membranes are used in the assays. This step could be eliminated by precisely determining the level of APP proteolytic products in a known cell culture of cells expressing APP. Thereafter the known level can be adjusted for in the assay, i.e., increases or decreases relative to the known background level could be determined by subtracting away the known background level. In order to perform the assay in this manner, it would, of course, be necessary to obtain cell membranes from a statistically significant number of recombinant cells which express a known level of APP and thereafter determining the background level of APP proteolytic products present in the membranes of these cells.

The assays may be performed in the presence or absence of BACE1 and/or other $\beta$-secretase(s).

In a preferred embodiment, the present invention provides an assay methodology for identifying compounds which have an effect on (preferably enhance) BACE2-mediated suppression of Aβ by promoting α-secretase-like cleavage, using synthetic substrates spanning residues comprising the α-secretase site of APP. Such substrates might include, for example, synthetic peptides or fluorogenic synthetic substrates. Read-outs of such an assay might include the generation of a smaller peptide fragment or by fluorescence resonance energy transfer (FRET) of the cleaved fluorescently tagged substrate.

3. Transgenic animal models

Compounds found to enhance or stimulate BACE2-mediated suppression of Aβ production can be further assayed in transgenic mammals. Transgenic animal models are well known in the art, and are described, for example, in Moran et al. *Proc. Natl. Acad. Sci. USA* 92: 5341–5345 (1995); Games et al. *Nature* 373: 523–527 (1995); Haiso et al. *Science* 274: 99–102 (1996), and in U.S. Pat. Nos. 5,387,742 and 5,912,410, the entire disclosures of which are hereby expressly incorporated by reference. Briefly, according to the method disclosed in the cited patents, cloned recombinant or synthetic DNA sequences related to the pathology of Alzheimer's disease are injected into fertilized mammalian eggs (preferably mouse eggs). The injected eggs are implanted in pseudo pregnant females and are grown to term to provide transgenic mice whose cells express proteins related to the pathology of Alzheimer's disease. The injected sequences are constructed having promoter sequences connected so as to express the desired protein in specific tissues of the transgenic mammal (most notably in nerve tissue). The proteins which are preferably ubiquitously expressed include: (1) Aβ-amyloid core precursor proteins; (2) Aβ-amyloid related precursor proteins; and (3) serine protease inhibitor. The transgenic mice provide useful models for studying compounds being tested for their usefulness in treating Alzheimer's disease and related conditions.

4. Compounds of the invention

Compounds of the invention encompass numerous chemical classes, including but not limited to the compounds described herein with known function. Novel methods are provided which employ compounds that are effective in enhancing or activating BACE2-mediated suppression or inhibition of Aβ production.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

Compounds for use in the method of invention may be small organic compounds having a molecular weight of more than 50 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomoleculese including, but not limited to: peptides, saccharides, fatty acids, steroids, purines, pyrimidines, derivatives, structural analogs or combinations thereof.

Further details of the invention will be illustrated in the following non-limiting Examples.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1 Materials and Methods Used in the BACE2 Assays

1. Cloning and coexpression of BACE and BACE2

BACE 2 was amplified from human brain cDNAs by Taq Polymerase Chain Reaction (PCR) using sequence information from PCT publication WO99/34004-A2. The amplified PCR product was cloned into pCRII -TOPO vector using TOPO TA cloning techniques (Invitrogen Co., San Diego, Calif.). Following restriction enzyme digestion, the BACE2 DNA fragment was sub-cloned into Not I and BamH I sites of mammalian expression vector pcDNA 3.1 (–). Restriction enzyme digestion pattern and sequence data confirmed the presence and orientation of the insert in pCDNA3.1(–)/BACE2. BACE was similarly cloned from human brain cDNAs using sequence information available from Vassar et al., [1999] ibid) to generate a mammalian expression vector pCDNA3.1 (–)/BACE.

Expression vectors containing BACE and BACE2 cDNAs were transfected into HEK293T cells in the presence of APP751sw or CT100 (Shoji et al., *Science* 258: 126–129 [1992]; Lichtenthaler et al., *Proc. Natl. Acad. Sci. USA* 96: 3053–3058 [1999]). Transfections were performed in 24 well plates using Lipofectamine Plus (Gibco/BRL, Bethesda, Md.) and DNA concentrations were kept constant by including non-specific DNA. Expression plasmids were tested for BACE and BACE2 expression by Western blotting. Cell culture supernatants were collected 48 hours and 72 hours post-transfection, and assayed for α-NTF, β-NTF and Aβ formation. β-NTF measurement was performed as described below. α-NTF was captured like β-NTF but was detected with biotinylated 2H3 (Johnson-Wood et al., *Proc. Nati. Acad. Sci. USA* 94: 1550–1555 [1997]). Aβ levels were determined by an ELISA using monoclonal antibodies 266 for capture and biotinylated 3D6 for detection (see Johnson-Wood et al., [1997] ibid for antibody epitope description). Aβ42, in contrast, was captured using 21F 12 and detected with biotinylated 3D6. Cell extracts prepared 72 hour post-transfection were separated by SDS-PAGE (Novex) and probed with CT695 (Zymed) for APP and CTFs as well as with an Aβ specific monoclonal antibody WO2 (kindly provided by K. Beyreuther; Ida et al., *J. Biol. Chem.* 271: 22908–22914 [1996]). Alternatively, co-transfection experiments using APP751sw and BACE or BACE2 were performed in the human neuroblastoma cell line, SK-N-MC, available from the American Type Culture Collection (ATCC).

2. Membrane Preparations

Membrane preparation is the first step in the isolation and purification or enrichment of β-secretases (BACE or BACE2) and the substrate (APP) since both of them are expressed as membrane integral proteins. Membrane preparations were generated from human embryonic kidney 293 cells (HEK293) expressing the 751 form of APP carrying the "Swedish" AD mutation (293/751sw). However, the protocol described below can be used for any cell type with only a minor modification. Cells were stored as cell pellets at −80° C. until used for the preparation.

Approximately 70–100 gram of cells (wet weight) were routinely used to generate 50–100 ml of enzyme substrate complex/mixture from membrane extracts. The cells were thawed and were resuspended through different iterations in a total volume of 12–15×vol/gram wet weight of TE/1X protease inhibitor cocktail (PIC) buffer [20 mM Tris-HCl/5 mM EDTA pH 8.5 (TE) with 1X PIC (1X PIC: 10 µM leupeptin, 1 µM aprotinin and 1 µM pepstatin, Boehringer Mannheim). Initially, the pellet was resuspended in ~6–9× vol/gram wet weight and homogenized using a tissumizer (IKA Labortechnik, Staufen, Germany) at medium setting for three times one minute with intermittent cooling on ice. The homogenate was then distributed into different 50 ml Falcon tubes and was centrifuged for 10 minutes at 1500 rpm in a table centrifuge (Sorvall) at 4° C. After the centrifugation, the supernatant corresponding to a PNS (post-nuclear supernatant) was carefully removed and pooled into a fresh tube. In order to avoid disturbing the relatively loose pellet, approximately 10 ml of material were left in each tube including the pellet that contained unbroken cells and nuclei. The pellet and remaining supernatant was pooled and resuspended in the remainder of the homogenization buffer. The suspension was then subjected to another round of homogenization with the tissumizer followed by centrifugation and supernatant collection as described above. The resulting PNS was pooled with the previously saved material. If deemed necessary, an additional round of homogenization was included or the previously centrifuged material was spun again to recover all the supernatant efficiently. The membranes were then recovered as a pellet by centrifugation of the pooled PNS at 28,000 rpm (~65, 000×g) in a Ti45 rotor (Beckman, Palo Alto, Calif.) for 30–40 min at 4° C.

Membrane preparations as prepared above were treated with a mild detergent to reduce, preferably to undetectable levels, background APP proteolytic products. The membrane pellet was resuspended sequentially in a total of 12×vol/gram wet weight of TE/1X PIC in the presence of a final concentration of 0.02% saponin (added from a 0.5% saponin stock solution made in distilled water). The pellet was homogenized on ice by 13–18 strokes in a Kontes glass tissue homogenizer with a tight pestle (0.013–0.14 mm clearance). Treatment with the mild detergent saponin permeabilizes the membranes and thus releases lumenal soluble proteins. In particular, this preferably reduces, to undetectable levels, any background APP proteolytic products, such as β-NTF. Following homogenization of the membranes on ice, the suspension was centrifuged in a Ti45 rotor at 28,000 rpm (~65,000×g) for 30–40 minutes. The saponin extract containing β-NTF was stored at −80° C. until it was further purified over a Q-HP column (similarly to the membrane extract described below) and the resulting fractions containing β-NTF were aliquoted and stored at −80° C. for use as a standard in ELISA. The pellet after the saponin extraction was resuspended again in TE/1X PIC, 0.02% saponin and treated as described, and this step was repeated until the membranes were washed in a total of 12×vol/gram cell paste.

Following the saponin extraction, the final membrane pellet (P2 pellet) was routinely frozen at −80° C. until further use. When needed, the frozen P2 pellet was thawed and resuspended in TE/1X PIC. Triton X100-R was added to a final concentration of 0.3% and the suspension was dounced on ice at least 12 times in a Kontes glass tissue homogenizer with a tight pestle (0.013–0.14 mm clearance). After the material had been suspended well, the solution was centrifuged at 32,000 rpm (~100,000×g) for 45–60 minutes at 4° C. The solubilized membrane supernatant was collected, and the pellet discarded. The solubilized Triton X100 extract was then filtered through a 0.45 µm bottle-top filter to remove insoluble material (Schleicher & Schuill) and was partially purified on a 25 ml Q-HP Sepharose column (Pharmacia, Stamford, Conn.) in the following manner.

The detergent-treated membrane preparations from the above step were partially purified using a Q-HP Sepharose chromatography column (Pharmacia, Stamford, Conn.). The Q-HP column was equilibrated with 5–10 column volumes (CVs) of equilibration buffer [20 mM Tris/EDTA pH 8.5, 0.05% Triton X100-R] and the extract was loaded at 5 ml/minutes. The column was then washed with 5 CVs of equilibration buffer to remove non-specifically bound proteins. Proteins including APP and β-secretase were eluted from the column with a linear gradient from 0–1M NaCl in equilibration buffer [TE, 0.05% Triton X100-R] over 5 CVs and ~8 ml fractions were collected. 1×PIC was added to the collection tubes prior to the run.

The total protein concentration for each sample was determined using a BCA protein test (Pierce, Rockford, Ill.), and a protein profile was also determined for the rinses and the elution. Alternatively, protein was followed with a UV monitor. Samples were run on an SDS-polyacrylamide gel for Western Blot analysis, and blotted with pAb369, an antibody which recognizes the C-terminus of APP (Gouras et al. *Proc. Natl. Acad. Sci. USA* 97: 1202–1205 [2000]). The saponin extract of washes was also blotted to analyze the βNTF using AF-20 series antibodies or equivalent. βNTF-specific antibodies were generated against the neoepitope produced by β-secretase cleavage of APP. The antibodies were generated against synthetic peptides, ISEVNL in the case of swedish isoform or ISEVKM in the case of wt substrate. The peptides were conjugated to a protein carrier via the N-terminal cysteine on the peptide, and used to immunize rabbits according to standard procedures. The resulting antisera were affinity purified using the peptide immunogens.

Individual fractions were then assayed for the presence of APP using an ELISA as well as for the presence of β-secretase using the native substrate assay as described below. Fractions containing APP and β-secretase were pooled as APP/β-secretase complex/mixture, aliquoted and stored at −80° C. for future use.

3. Partial Purification of APP Substrates

A partial purification approach to obtain APP751sw or APP751wt substrate devoid of endogenous β-secretase activity is presented below. Expression vector containing APP751sw or APP751wt cDNA in pcDNA3.1 (commercially available from Invitrogen) was transiently transfected into HEK293 cells according to standard procedures. Transient transfection of APP751sw improved the separation since a significantly higher ratio of substrate to enzyme could be obtained. Cells were transfected in roller bottles by a transfection method recommended by the manufacturer using FuGene 6 (Boehringer Mannheim). The cells were harvested and the equivalent of ~5–10 gms of cell paste was subjected to detergent extraction using the protocol described above. The detergent extract separated on a 1 ml Q- HP Sepharose column, as described above, contains both β-secretase and APP751 sw. The APP751 sw containing fractions were then pooled and the pool was diluted ~8–10 fold with equilibration buffer [20 mM Tris/EDTA pH 8.5, 0.05% Triton X100-R] to reduce the salt from the previous chromatography step. The material was then loaded onto a Mono Q column that had been equilibrated. Non-specifically bound proteins were washed with 10 CVs of equilibration buffer and proteins were eluted with a 15 CV linear gradient from 0–1 M NaCl in equilibration buffer. Again, fractions were analyzed for the presence of APP751 sw as described in earlier. The β-secretase activity was assayed with exogenously added APP751sw substrate. This was necessary since otherwise β-secretase would not have been detectable in fractions that were very limited in APP751sw substrate. The mono Q step allowed the separation of the APP751sw substrate from the bulk of the endogenous β-secretase. Based on this procedure, we have routinely obtained APP751sw at concentrations of ~4–6 μg/ml and use ~3–8 μl per reaction to determine the β-secretase activity when substrate needs to be added back to the reaction mixture. The β-secretase activity devoid of substrate from this column was also pooled for additional experiments.

Th C-terminal 100 amino acids of APP can also be prepared as a substrate for BACE2 activity. This fragment has been successfully expressed in bacteria with an epitope tag at the C-terminus to facilitate purification (Higaki et al. *J. Biol. Chem.* 271: 31885–31893 [1996]).

4. Generation of BACE2 Asp Mutant

A single D110A BACE2 mutant was created in the parent vector pcDNA3.1 (–)/BACE2 using Stratagene's Quick-Change site-directed mutagenesis kit. The following primers were used to introduce the change and the mutation was subsequently confirmed by DNA sequencing.

(SEQ ID NO: 3)
5'-GCTACAGATTCTCGTTGCCACTGGAAGCAGTAACTTTG-3'

(SEQ ID NO: 4)
5'-CAAAGTTACTGCTTCCAGTGGCAACGAGAATCTGTAGC-3'

5. Preparation of BACE and BACE2 Specific Antibodies

Polyclonal antisera specific for BACE and BACE2 were generated in rabbits against C-terminal peptides of BACE (CLRQQHDDFADDISLL, SEQ ID NO: 5) and BACE2 (CQRRPRDPEVVNDESS, SEQ ID NO: 6). The peptides were conjugated to KHL and antibodies were generated according to standard procedures (Sigma Genosys).

6. Pulse-Labeling and Immunoprecipitation

Forty eight hours post-transfection, HEK293T cells were labeled for 15 minutes with 200 μCi Promix L [$^{35}$S] in vitro cell labeling mix (Amersham) and chased for up to 90 minutes according to standard procedures. APP CTFs were immunoprecipitated with antibodies 369 (Cai et al., *Science* 259: 514–516 [1993]). For immunoprecipitations of Aβ and p3 from conditioned medium, HEK293T cells were labeled for 5 hours with 300 μCi Promix L [$^{35}$S] in vitro cell labeling mix (Amersham) 48 hours post-transfection. Aβ40 and Aβ42 as well as the corresponding p3 species were immunoprecipitated with monoclonal antibodies 1702.1 and 108.1, respectively (Higaki et al., *J. Med. Chem.* 42: 3889–3898 [1999]).

7. Assay of β-secretase Activity and Estimation of βNTF and APP by ELISA

The β-secretase assay consists of two different parts, an incubation or reaction phase to generate β-NTF and an ELISA part to capture and measure the β-NTF generated by β-secretase. The β-secretase ELISA was performed as follows. Each well of a 96 well plate containing a flat bottom (high protein binding, Corning, N.Y.) was coated with 100 μl of the monoclonal capture antibody 8E5 (at ~8–10 μg/ml) (Johnson-Wood et al. *Proc. Natl. Acad. Sci. USA* 94: 1550–1555 [1997]). The plate was then covered with parafilm and incubated overnight at 4° C. or alternatively for 2 hours at 37° C. Following incubation, any excess liquid was removed, wells blotted dry and incubated with 150 μl of blocking buffer (0.1% BSA/PBS) per well at 37° C. or room temperature for 1–2 hours.

Membrane extracts of naive HEK293 cells or HEK293 cells expressing BACE or BACE 2 were incubated in the presence of partially purified APP751sw or APP751wt in assay buffer (50 mM KPi, 5 mM EDTA, 0.02% Triton-X-100, 10 μM cardiolipin, pH 4.5) in a final volume of 100 μl. The reaction samples were incubated at 37° C. for 6–18 hours and were then stopped by placing the samples at –20° C.

After removing blocking buffer, the coated plates were blot dried. To one set of wells, different volumes (e.g. 0, 0.5, 1, 2, 4, 8, and 10, μl) of the Saponin wash from the membrane preparation were added. These were diluted to a final volume of 100 μl with dilution buffer and served to establish the linearity of the assay (typically in the OD 450 nm range from 0.06 to 1.2).

To another set of remaining wells, 50 μl of a β-secretase reaction performed as described above was added, followed by the addition of dilution buffer (50 μl) to make up the volume to 100 μl/well. The ELISA plate was incubated at room temperature for 1–2 hours. Following incubation, the plate was washed three times with 200 μl of Wash Buffer (50 mM Tris-HCl pH 7.5, 150 mM NaCl, 0.05% Tween-20), and blot dried. Alternatively, PBS, 0.05% Tween-20 can be used as wash buffer. One hundred μl of 1:5000 dilution of the affinity purified anti-β-NTF AF-#20 antibodies in Antibody/Conjugate Buffer [PBS, 2% BSA, 0.05% Tween-20] was then added to each well and the plate incubated at room temperature for 1 hour. AF#20 specifically recognizes the neoepitope produced upon β-secretase cleavage of APP. The plate was again washed three times with wash buffer, and excess liquid was removed between washes.

One hundred μl of a 1:5000 dilution of a goat anti rabbit IgG-HRP in Antibody-Conjugate Buffer was then added to each well, and the plate incubated at room temperature for one hour. After the secondary antibody incubation, the plate was washed three times with wash buffer. One hundred μl of TMB/H$_2$O$_2$ (Sigma) that had been brought to room temperature during the previous incubation was then added to each well. During the development of 5–20 minutes, the plate was covered with aluminum foil and stored in the dark. After sufficient blue color had developed, the reactions were stopped by adding 100 μl of 5N H$_2$SO$_4$ to each well, and the amount of βNTF was determined by reading the plate at 450 nm in a Softmax spectrophotometer.

To determine the substrate (APP) levels in these fractions, either 10 μl of the −20° C. reaction mix or 10 μl from the fractions directly were added onto ELISA wells coated with the 8E5 antibody and blocked as described above. The samples were diluted with 90 μl dilution buffer and the ELISA was performed basically as described above except that the detection system was slightly different. APP was detected using a primary biotinylated monoclonal 2H3 antibody at a dilution of 1:2000 (Johnson-Wood et al., [1997] ibid), followed by a streptavidin-HRP conjugate (Zymed) used at 1:5000.

Example 2 BACE2 possesses β-secretase activity in vitro

To determine whether BACE2 possesses β-secretase activity, we reconstituted the cleavage of APP751sw and APP751wt at the β-secretase site in a cell-free assay. Equal amounts of membrane extracts from either mock, BACE or BACE2 transfected HEK293 cells were incubated with partially purified full length APP751 sw or APP751wt for the indicated times. The formation of β-NTF was then determined using the respective β-NTF specific ELISA as described in General Methodology.

Extracts from both BACE and BACE2 transfected cells showed a time-dependent increase in β-NTF formation using APP751sw as a substrate (FIG. 1a). This activity was absent from mock-transfected extracts within the 2 hour incubation time. Endogenous secretase levels as present in the mock-treated extracts required incubation times between 12 and 16 hours in order to detect sufficient β-NTF levels in this assay (data not shown). As a consequence, all detectable β-secretase activity in the respective extracts was due to the overexpressed proteins, BACE and BACE2, respectively. In addition, when combining different amounts of BACE and BACE2 extracts in the assay, the effect on β-NTF formation was additive (data not shown).

BACE2 also cleaved APP751wt to a similar extent as BACE (FIG. 1b). As expected from APP751wt being a significantly weaker substrate than APP751sw (Citron et al., [1992] ibid; Cai et al., [1993] ibid), incubation times were extended up to 8 hours. In contrast to the previous notion that BACE is the major β-secretase (Vassar et al., [1999] ibid; Sinha et al,[1999] ibid; Hussain et al., [1999] ibid; Yan et al., [1999] ibid; Lin et al.,[2000] ibid; Bennet et al., [2000] ibid), BACE2 appears to be quite efficient at processing APP at the β-secretase site in a cell-free environment. Thus, BACE2 might indeed be a functional homolog of BACE.

Figure 2:
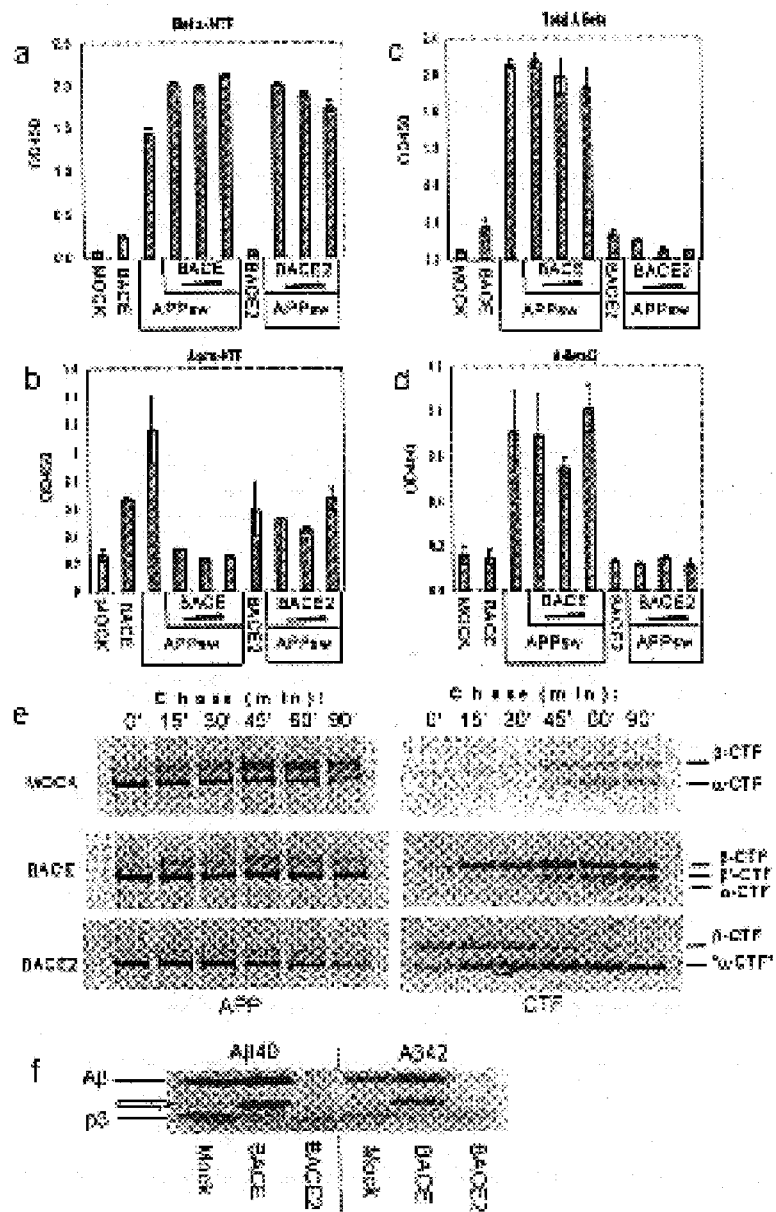
FIG. 2. BACE2 leads to alternative processing of APP and suppresses Aβ formation in HEK293T cells. Different amounts of BACE and BACE2 cDNA were co-transfected with constant levels of APP751sw plasmid and conditioned medium was analyzed for β-NTF (a), α-NTF (b), total Aβ (c) and Aβ42 (d) 72 hours post-transfection. BACE2 shows some β-secretase activity in vivo while dramatically suppressing the production of Aβ40 and Aβ42. The metabolism of APP CTFs was analyzed in a parallel pulse-chase experiment (e). Transfected cells were labelled for 15 minutes with 200 µCi Promix L [$^{35}$S] (Amersham) and chased for up to 90 minutes. APP and CTFs were immunoprecipitated as described. Full length mature and immature APP (APP) as well as bands corresponding to β-CTF , alternatively cleaved β'-CTF and α-CTF are shown. The formation of Aβ and p3 was analyzed in a pulse-labeling experiment (f). Transfected cells were labeled for 5 hours with 300 µCi Promix L [$^{35}$S] (Amersham) and conditioned medium was precipitated with antibodies directed against the C-terminal residues of Aβ40 and Aβ42, respectively, that also recognize the corresponding p3 forms. The arrow indicates an additional Aβ species derived from cleavage of the β'-CTF in BACE transfected cells.

Example 3 BACE2 Overexpression Leads to Suppression of Aβ Formation in HEK293T Cells Given the ability of BACE2 to cleave APP at the β-secretase site in vitro, we investigated the role of BACE2 in HEK293T cells relative to BACE. Variable amounts of BACE2 or BACE expression plasmids were co-transfected with constant amount of DNA encoding APP751sw substrate cDNA. Cell supernatants were collected 48 hours or 72 hours post-transfection and analyzed for α-NTF, β-NTF, total Aβ and Aβ42 as described in Genenral Methodology. Expression of APP751 sw alone led to a significant increase in β-NTF, α-NTF, total Aβ and Aβ42 (FIGS. 2a–d) compared to mock-transfected cells. This suggested that endogenous secretases were not limiting for β-NTF or Aβ formation under these conditions. When BACE was expressed in addition to APP751 sw, β-NTF levels (FIG. 2a) were further increased as expected from earlier reports (Vassar et al, [1999] ibid; Sinha et al., [1999] ibid; Yan et al., [1999] ibid). As a consequence, α-NTF levels were proportionally reduced (FIG. 2b). Under these conditions, Aβ production was not significantly stimulated. This was most likely due to the fact that overexpressed APP751sw was in excess and was already very efficiently cleaved by endogenous BACE (compare mock versus APP751 sw alone). BACE effects on Aβ formation have been reported to be variable (Vassar et al., [1999] ibid; Sinha et al,[1999] ibid; Hussain et al., [1999] ibid; Yan et al, [1999] ibid; Lin et al,[2000] ibid) and thus it appears that additional factors such as γ-secretase might become limiting.

Figure 4:
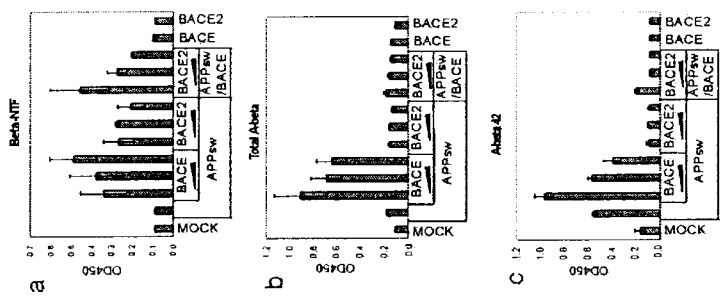
FIG. 4. BACE2 shows β-secretase activity and suppresses Aβ formation in SK-N-MC cells. Different amounts of BACE and BACE2 cDNA were co-transfected with constant levels of APP751sw plasmid and conditioned medium was analyzed for—NTF (a), total A (b) and Aβ42 (c) 72 hours post-transfection.

When co-transfecting BACE2 with APP751sw, the effect on β-NTF levels was very similar to that of BACE suggesting that BACE2 had some β-secretase activity in vivo. In fact, the levels of α-NTF and β-NTF generated by BACE2 and BACE were inversely proportional to each other and added up to basically the same total OD values as in cells transfected with APP751sw alone (total OD ~2.59 for APP751sw alone, ~2.5 with BACE2, and ~2.3 with BACE). The combined values of α- and β-NTF for BACE was slightly lower since the β-NTF assay had reached saturation. The different ratios of α- and β-NTF values under the different transfection conditions are consistent with the competition of β-secretase and α-secretase for the same substrate (Skovronsky et al. (2000), *J. Biol. Chem.* 275: 2568–2575). The slightly higher levels of α-NTF in conditioned medium from BACE2 versus BACE transfected cells reflects in part the fact that BACE2 is the weaker β-secretase (FIG. 2b, see FIG. 4). In contrast to BACE, BACE2 expression resulted in the striking reduction of total Aβ and Aβ42 to levels found in mock-transfected cells (FIG. 2c, d). Thus, BACE2 suppressed Aβ production without significantly affecting the formation of either β- or α-NTF.

To analyze the metabolism of APP as a consequence of BACE or BACE2 overexpression we performed a parallel pulse-chase experiment (FIG. 2e). HEK293T cells transfected as above were pulse-labeled and chased for up to 90 minutes and APP and CTFs were immunoprecipitated. Both BACE and BACE2 showed CTF turnover that was significantly different from that of mock-transfected cells. As expected, BACE expression resulted in the accumulation of β-CTF . An alternative β-secretase related cleavage product (β'-CTF) was also formed consistent with previous reports (Vassar et al., *Science* [1999] ibid; Higaki et al., *Neuron* 14: 651–659 [1995]). Consistent with its β-secretase activity, BACE2 overexpression led to a significant initial increase in β-CTF levels compared to mock-transfected cells. In contrast to BACE, β-CTF formation was more moderate and β-CTF did not accumulate over time, nor was any β'-CTF formed. Instead, we observed the strong accumulation of a cleavage product that based on size and gel migration corresponded to α-CTF. Thus, BACE2 initially enhanced β-secretase cleavage and instead of being processed to Aβ, most of the resulting β-CTF appeared to have been further converted into α-CTF. In general, BACE2 might have increased the overall APP turnover. To determine whether BACE affected γ-secretase activity, we determined whether p3 could be formed. We transfected HEK293 cells as in FIG. 2e and labeled them for 5 hours with Promix L [$^{35}$S]. Aβ from conditioned medium was then precipitated with antibodies directed against the C-terminal residues of Aβ40 and Aβ42, respectively, that also recognize p3 (FIG. 2f). Consistent with the ELISA results, BACE2 expression interfered with the formation of both Aβ40 and Aβ42. Interestingly, p3 formation was very similar to mock-transfected cells and thus p3 levels were not significantly affected by BACE2. Taken together, BACE2 expression leads to alternative processing of APP that precludes Aβ formation.

Figure 3:
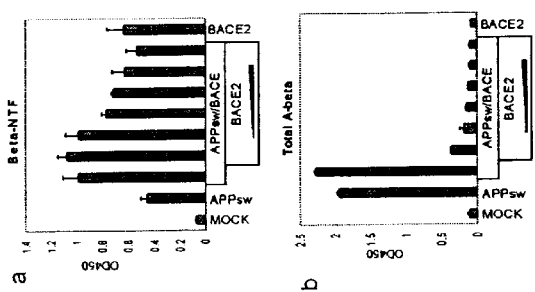
FIG. 3. Increasing doses of BACE2 differentially affect cleavage at the β-secretase site and Aβ formation. Constant amounts of BACE and increasing amounts of BACE2 were co-transfected with APP751sw into HEK293T cells. Conditioned medium was analyzed for β-NTF (a) and Aβ (b) formation as described.

In an independent experiment, we addressed whether BACE2 competed with the ability of BACE to cleave APP at the β-secretase site. HEK293T cells were co-transfected with constant amounts of APP751sw and BACE, and increasing levels of BACE2. β-NTF and Aβ levels were then measured in culture supernatant (FIG. 3). As seen before, BACE2 expression led to a dramatic dose-dependent reduction in Aβ levels (FIG. 3b). Interestingly, Aβ suppression was very pronounced even at the lowest BACE2 concentration. This suggests that relatively little BACE2 is required for this effect implying an enzymatic mechanism. BACE2 reduced the ability of BACE to form β-NTF in a dose-dependent manner, however, the effect was significantly less pronounced compared to the Aβ suppression (FIG. 3a). BACE and BACE2 appeared to compete for the substrate and thus the effect on β-NTF might rather be steric. In particular, if BACE2 is a less efficient β-secretase in competing with BACE for substrate, it would reduce the overall β-secretase cleavage efficiency (see also FIG. 4). However, this reduction is insufficient to account for the Aβ reduction with BACE2.

Example 4 BACE2 Modulates Aβ Levels in Neuronal SKN Cells

We further assessed the modulatory effect of BACE2 on Aβ formation using a human neuroblastoma cell line, SK-N-MC. In contrast to HEK293 cells, expression of APP751sw alone did not result in a significant increase in the formation of either Aβ or β-NTF suggesting that either endogenous secretases or exogenous substrate were more limiting under these conditions (FIG. 4). As a consequence, we were able to see a very pronounced increase in both β-NTF and Aβ upon BACE expression (FIGS. 4a, b). BACE2 also showed β-secretase activity in vivo that was more easily scored in the neuronal cells due to the lower β-NTF levels that were present when APP751sw was transfected alone. As seen in HEK293T cells, BACE2 competed with the ability of BACE to stimulate β-NTF formation (FIG. 4a). Consistent with HEK293T cells, BACE2 expression also led to a significant reduction of Aβ in SK-N-MC cells confirming that BACE2 suppresses Aβ levels in different cell types including neuronal cells (FIGS. 4b, c).

The results thus confirm that BACE2 modulates Aβ levels in various cell types including neuronal cells. Furthermore, weak β-secretase activity of BACE2 was more apparent in SK-N-MC cells. The present study further confirms that BACE2 competes with the ability of BACE to form β-NTF. Based on these findings, it appears that BACE2 competes with BACE for APP substrate without processing APP as efficiently.

Figure 5:
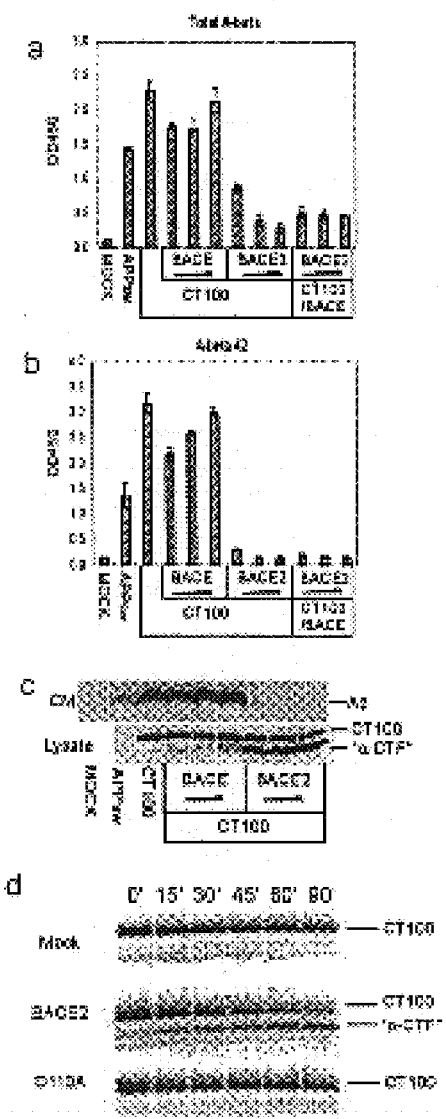
FIG. 5. Prior β-secretase cleavage is not required for Aβ suppression by BACE2. BACE and BACE2 were co-transfected with CT100, an APP construct that mimics prior β-secretase cleavage and total Aβ (a) and Aβ42 (b) were measured in conditioned medium by ELISA. The conditioned medium was further subjected to Western blotting for the detection of Aβ and CTFs (c) as described. The metabolism of CT100 was analyzed in a parallel pulse-chase experiment (d). Cells were labeled for 15 minutes with 200 µCi Promix L [35S] (Amersham) and chased for up to 90 minutes. CTFs were immunoprecipitated as described. CT100 as well as the α-CTF-like band are shown.

Example 5 Prior β-secretase Cleavage is not Required for the Modulatory Effect of BACE2 on Aβ Levels As described above, BACE2 expression resulted in the accumulation of APP CTFs concomitant with the reduction of Aβ levels. This effect prompted investigation into whether β-secretase cleavage was required for Aβ suppression. The effects of BACE2 on the metabolism of the C-terminal 100 amino acids of APP (CT100), a construct that mimics prior β-secretase cleavage (Shoji et al., Science 258: 126–129 [1992]), was analyzed. When CT100 was expressed in HEK293T cells, Aβ levels were significantly increased over mock-transfected cells (FIG. 5A). As expected, additional BACE copies did not affect the levels of Aβ under CT100overexpression conditions. Co-expression of BACE2 and CT100 resulted in the dramatic suppression of total Aβ as well as Aβ42 levels (FIGS. 5a, b). Thus, the capacity of BACE2 to suppress Aβ formation does not require prior β-secretase cleavage. The dramatic reduction in Aβ formation was confirmed by Western blotting of conditioned medium and the CTFs in the lysate (FIG. 5c). BACE2 also led to the accumulation of a fragment that corresponded in size to α-CTF. At steady-state, this was accompanied by a partial reduction in CT100 which corresponds to β-CTF confirming that β-CTF could be converted to α-CTF under these BACE2 conditions. To confirm that there was a precursor-product relationship between β-CTF (i.e., CT100) and the α-like CTF that accumulated upon BACE2 overexpression, a pulse-chase analysis was performed. HEK293 cells were transfected with CT100 alone or CT100 with BACE2. Cells were readiolabeled with $^{35}$S-methionine/cysteine for 15 minutes after which the medium containing radiolabel was removed and replaced with standard medium. The cells were then incubated for 90 minutes. Over this 90-minute period, samples were taken and assessed for CTFs by immunoprecipitation. Under these CT100 transfection conditions, endogenous APP was negligible in the formation of CTFs. While CT100 was fairly stable in mock-transfected cells, BACE2 expression yielded a pattern of CTFs that was identical to that observed when APP was co-transfected (FIG. 5d). Again, BACE2 resulted in the accumulation of the α-like CTF, clearly indicating that it was derived from CT100. This effect was rescued when a critical aspartate residue was mutated in BACE2 (D110A in FIG. 5d; also see below). This indicates that BACE2 has α-secretase-like activity. Taken together, these data indicate that the ability of BACE2 to suppress Aβ production reflects enhanced α-secretase-like activity that is independent of prior β-secretase cleavage. This α-secretase-like activity of BACE2 promotes the non-amyloidogenic processing of APP or APP fragments and reduces the production of Aβ.

Example 6 Mutation of a Critical Aspartate Residue in BACE2

Figure 6:
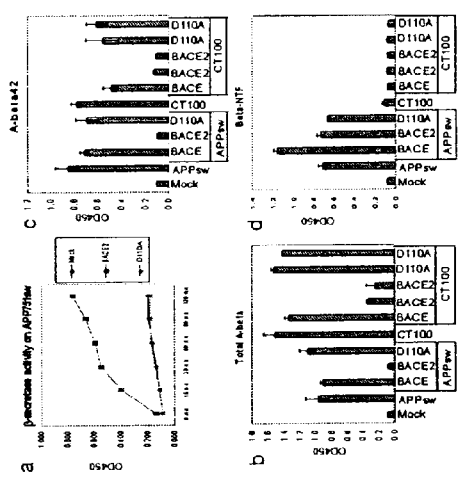
FIG. 6. Mutation of the conserved aspartate residue in BACE2 abolishes β-secretase activity in vitro and reverses the effect on Aβ formation in vivo. Membrane extracts from BACE2, BACE2 D110A, or mock-transfected HEK293T cells were separated on Q-HP-Sepharose and fractions were reconstituted with APP751sw substrate for 2 hours at 37° C. β-NTF formation was monitored as described (a). BACE2 D110A and wildtype BACE2 were co-transfected with APP751sw or CT100 in HEK293T cells. Total Aβ (b), Aβ42 (c), and β-NTF (d) were determined in conditioned medium as described.

It was of interest to determine whether BACE2-mediated suppression of Aβ formation required its aspartyl protease activity. This issue was addressed by mutating one of the critical aspartate residues (D100A) in BACE2 and co-transfecting cells with this mutant BACE2 and APP751sw. As expected from the homology to BACE (Yan et al., [1999] ibid; Lin et al., [2000] ibid; Acquati et al., [2000] ibid; Bennett et al., [2000] ibid), extracts derived from BACE2 D110A transfected cells lost their ability to cleave at the β-secretase site in vitro (FIG. 6a). In addition we assessed the effect of the BACE2 D110A mutant on Aβ and β-NTF levels in vivo. Interestingly, BACE2 D110A clearly reversed the suppression of Aβ production (FIG. 6b, c). As a consequence, the α-like CTF did not accumulate (as shown in FIG. 5d). This demonstrates that the effect of BACE2 is based on an enzymatic mechanism as suggested above. In contrast, BACE2 D110A appeared to compete as well if not slightly more effectively with BACE to form β-NTF, again suggesting that the effect at the β-secretase site might be allosteric (FIG. 6d). The BACE2 D110A mutant was also shown to be unable to convert APP CT100 to an α-CTF-like fragment indicating that BACE2 enzymatic activity is required for its α-secretase-like cleavage.

In summary, results disclosed herein indicate that BACE2 possesses weaker β-secretase activity than BACE and competes with BACE in an allosteric manner. This competition is further enhanced when mutating the critical aspartate of BACE2 thereby eliminating its β-secretase activity. We also demonstrated that BACE2 interferes with Aβ production by an enzymatic mechanism that depends on its proteolytic activity. BACE2 appears critically involved in APP processing towards the non-amyloidogenic pathway by promoting an cc-secretase-like cleavage which results in reduced Aβ generation.

There are four main possibilities how BACE2 can affect Aβ production. First, BACE2 could interfere with β-secretase activity. Even though BACE2 seems to somewhat compete with exogenous BACE for cleavage at the β-secretase site, this scenario seems rather unlikely. BACE2 is clearly capable of processing APP at the β-secretase site and in fact increases β-NTF and β-CTF formation relative to mock-transfected cells. Second, BACE2 might negatively regulate or inactivate γ-secretase or presenilin proteins that are essential for γ-secretase activity (Selkoe et al., *Proc. Natl. Acad. Sci. USA* 97: 5690–5692 [2000]). The accumulation of CTFs in BACE2 overexpression is somewhat reminiscent of blocking γ-secretase through inhibitors or mutations of critical aspartates in presenilin (Higaki et al., [1995] ibid; Wolfe et al., *J. Med. Chem.* 41: 6–9 [1998]; Wolfe et al., *Nature* 398: 513–517 [1999]). In contrast to a simple γ-secretase inhibition, however, BACE2 expression resulted in the unusual accumulation of mainly the α-CTF like cleavage product. Furthermore, levels of p3 were not significantly affected by BACE2 suggesting normal γ-secretase activity. Alternatively, it is conceivable that BACE2 prevents APP from reaching the subcellular compartment in which γ-secretase resides, although it remains unclear how this would involve a proteolytic event. Third, BACE2 overexpression might alter APP processing. Fourth, BACE2 has or enhances cc-secretase activity. We observed that processing of APP in BACE2 transfected cells proceeded via initial β-site cleavage and ultimately resulted in the accumulation of a fragment that corresponded in size and gel migration to α-CTF. There was a direct precursor-product relationship between the β-CTF and the α-CTF like fragment that was demonstrated using CT100 as the substrate.

Since BACE2 appears to be critically involved in modulating Aβ production, its levels in different tissues might constitute an important factor in regulating Aβ deposition. In this respect, it is noteworthy that BACE2 mRNA is not very abundant in brain (Bennett et al., [2000] ibid) where BACE is expressed well (Vassar et al., [1999] ibid).

All references cited throughout the present disclosure and all references quoted therein are hereby expressly incorporated by reference. While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step of steps, to the objective, spirit and scope of the present invention. All such modifications are intended to be within the scope of the claims appended herein.

What is claimed is:

1. A method of modulating the enzymatic production of β-amyloid peptide (Aβ) from β-amyloid precursor protein (APP) or a fragment thereof, comprising contacting said APP or APP fragment with a BACE2 polypeptide or an agonist or antagonist thereof.

2. The method of claim 1 wherein said APP is a native sequence human APP.

3. The method of claim 2 wherein said APP is the 695-amino acid isotype.

4. The method of claim 2 wherein said APP contains the Swedish mutation.

5. The method of claim 1 wherein said APP fragment is β-CTF.

6. The method of claim 1 wherein said BACE2 is a native sequence BACE2 polypeptide.

7. A method of inhibiting the formation of a β-amyloid peptide (Aβ) from β-amyloid precursor protein (APP) or a fragment thereof, comprising contacting said APP or APP fragment with a BACE2 polypeptide or an agonist thereof.

8. The method of claim 7 wherein said APP is a native sequence human APP.

9. The method of claim 8 wherein said APP is the 695-amino acid isotype.

10. The method of claim 8 wherein said APP contains the Swedish mutation.

11. The method of claim 7 wherein said APP fragment is β-CTF.

12. The method of claim 7 wherein said BACE2 is a native sequence BACE2 polypeptide.

13. The method of claim 7 which is performed in the presence of an α-secretase activity.

14. The method of claim 7 which is performed in the presence of a γ-secretase activity.

15. The method of claim 7 which is performed in the presence of a β-secretase activity other than BACE2.

16. The method of claim 15 wherein said β-secretase activity in due to the presence of an enzyme having a pH optimum at about pH 6.5–7.0, and an estimated molecular weight of about 32–39 kDa as calculated from radiation inactivation analysis of HEK293 cell membrane extracts, or about 20–26 kDa as calculated from radiation inactivation analysis of human brain samples, with a candidate compound.

17. The method of claim 15 wherein said β-secretase activity is due to the presence of a β-secretase enzyme having a pH optimum at about pH 4.5–5.0 and an estimated molecular weight of about 50–60 kDa as calculated from radiation inactivation analysis of HEK293 cell membrane extracts or human brain samples (BACE1).

18. The method of claim 7 wherein said BACE2 is in isolated form.

19. The method of claim 7 wherein said BACE2 is in immobilized or cell bound form.

20. The method of claim 7 wherein the APP or APP fragment is contacted with an agonist of BACE2.

21. The method of claim 20 wherein said agonist stimulates the production of BACE2.

22. The method of claim 20 wherein said agonist enhances the activity of BACE2.

23. The method of claim 20 wherein said agonist mimics the activity of BACE2.

24. The method of claim 20 wherein said agonist is a small molecule.

25. A method of inhibiting the release of a full-length β-amyloid (Aβ) polypeptide from ±3-amyloid precursor protein (APP) or a fragment thereof, comprising cleaving said APP or APP fragment by a BACE2 polypeptide or an agonist thereof at a site interfering with β-secretase processing of said APP or APP fragment.

26. The method of claim 25 wherein said site is at or around the α-secretase cleavage site of native sequence APP or a fragment thereof.

27. The method of claim 26 wherein said site is within about 10 amino acids on either side of said βecretase cleavage site.

* * * * *

SEQUENCE LISTING

<160> NUMBER OF SEQ ID NOS: 6

<210> SEQ ID NO 1
<211> LENGTH: 1863
<212> TYPE: DNA
<213> ORGANISM: Homo sapiens
<220> FEATURE:
<221> NAME/KEY: CDS
<222> LOCATION: (109)...(1662)

<400> SEQUENCE: 1

```
cccatccctg cccgcagccc cgcgcgccgg ccgagtcgct gagccgcggc tgccggacgg        60
gacgggaccg gctaggctgg gcgcgcgccc ccgggccccg ccgtgggc atg ggc gca       117
                                                    Met Gly Ala
                                                     1 ctg gcc cgg gcg ctg ctg ctg cct ctg ctg gcc cag tgg ctc ctg cgc       165
Leu Ala Arg Ala Leu Leu Leu Pro Leu Leu Ala Gln Trp Leu Leu Arg
      5                  10                  15 gcc gcc ccg gag ctg gcc ccc gcg ccc ttc acg ctc ccc ctc cgg gtg       213
Ala Ala Pro Glu Leu Ala Pro Ala Pro Phe Thr Leu Pro Leu Arg Val
 20                  25                  30                  35 gcc gcg gcc acg aac cgc gta gtt gcg ccc acc ccg gga ccc ggg acc       261
Ala Ala Ala Thr Asn Arg Val Val Ala Pro Thr Pro Gly Pro Gly Thr
                 40                  45                  50 cct gcc gag cgc cac gcc gac ggc ttg gcg ctc gcc ctg gag cct gcc       309
Pro Ala Glu Arg His Ala Asp Gly Leu Ala Leu Ala Leu Glu Pro Ala
             55                  60                  65 ctg gcg tcc ccc gcg ggc gcc gcc aac ttc ttg gcc atg gta gac aac       357
Leu Ala Ser Pro Ala Gly Ala Ala Asn Phe Leu Ala Met Val Asp Asn
```

```
                    70                  75                  80
ctg cag ggg gac tct ggc cgc ggc tac tac ctg gag atg ctg atc ggg     405
Leu Gln Gly Asp Ser Gly Arg Gly Tyr Tyr Leu Glu Met Leu Ile Gly
     85                  90                  95 acc ccc ccg cag aag cta cag att ctc gtt gac act gga agc agt aac     453
Thr Pro Pro Gln Lys Leu Gln Ile Leu Val Asp Thr Gly Ser Ser Asn
100                 105                 110                 115 ttt gcc gtg gca gga acc ccg cac tcc tac ata gac acg tac ttt gac     501
Phe Ala Val Ala Gly Thr Pro His Ser Tyr Ile Asp Thr Tyr Phe Asp
                120                 125                 130 aca gag agg tct agc aca tac cgc tcc aag ggc ttt gac gtc aca gtg     549
Thr Glu Arg Ser Ser Thr Tyr Arg Ser Lys Gly Phe Asp Val Thr Val
            135                 140                 145 aag tac aca caa gga agc tgg acg ggc ttc gtt ggg gaa gac ctc gtc     597
Lys Tyr Thr Gln Gly Ser Trp Thr Gly Phe Val Gly Glu Asp Leu Val
        150                 155                 160 acc atc ccc aaa ggc ttc aat act tct ttt ctt gtc aac att gcc act     645
Thr Ile Pro Lys Gly Phe Asn Thr Ser Phe Leu Val Asn Ile Ala Thr
    165                 170                 175 att ttt gaa tca gag aat ttc ttt ttg cct ggg att aaa tgg aat gga     693
Ile Phe Glu Ser Glu Asn Phe Phe Leu Pro Gly Ile Lys Trp Asn Gly
180                 185                 190                 195 ata ctt ggc cta gct tat gcc aca ctt gcc aag cca tca agt tct ctg     741
Ile Leu Gly Leu Ala Tyr Ala Thr Leu Ala Lys Pro Ser Ser Ser Leu
                200                 205                 210 gag acc ttc ttc gac tcc ctg gtg aca caa gca aac atc ccc aac gtt     789
Glu Thr Phe Phe Asp Ser Leu Val Thr Gln Ala Asn Ile Pro Asn Val
            215                 220                 225 ttc tcc atg cag atg tgt gga gcc ggc ttg ccc gtt gct gga tct ggg     837
Phe Ser Met Gln Met Cys Gly Ala Gly Leu Pro Val Ala Gly Ser Gly
        230                 235                 240 acc aac gga ggt agt ctt gtc ttg ggt gga att gaa cca agt ttg tat     885
Thr Asn Gly Gly Ser Leu Val Leu Gly Gly Ile Glu Pro Ser Leu Tyr
    245                 250                 255 aaa gga gac atc tgg tat acc cct att aag gaa gag tgg tac tac cag     933
Lys Gly Asp Ile Trp Tyr Thr Pro Ile Lys Glu Glu Trp Tyr Tyr Gln
260                 265                 270                 275 ata gaa att ctg aaa ttg gaa att gga ggc caa agc ctt aat ctg gac     981
Ile Glu Ile Leu Lys Leu Glu Ile Gly Gly Gln Ser Leu Asn Leu Asp
                280                 285                 290 tgc aga gag tat aac gca gac aag gcc atc gtg gac agt ggc acc acg    1029
Cys Arg Glu Tyr Asn Ala Asp Lys Ala Ile Val Asp Ser Gly Thr Thr
            295                 300                 305 ctg ctg cgc ctg ccc cag aag gtg ttt gat gcg gtg gtg gaa gct gtg    1077
Leu Leu Arg Leu Pro Gln Lys Val Phe Asp Ala Val Val Glu Ala Val
        310                 315                 320 gcc cgc gca tct ctg att cca gaa ttc tct gat ggt ttc tgg act ggg    1125
Ala Arg Ala Ser Leu Ile Pro Glu Phe Ser Asp Gly Phe Trp Thr Gly
    325                 330                 335 tcc cag ctg gcg tgc tgg acg aat tcg gaa aca cct tgg tct tac ttc    1173
Ser Gln Leu Ala Cys Trp Thr Asn Ser Glu Thr Pro Trp Ser Tyr Phe
340                 345                 350                 355 cct aaa atc tcc atc tac ctg aga gac gag aac tcc agc agg tca ttc    1221
Pro Lys Ile Ser Ile Tyr Leu Arg Asp Glu Asn Ser Ser Arg Ser Phe
                360                 365                 370 cgt atc aca atc ctg cct cag ctt tac att cag ccc atg atg ggg gcc    1269
Arg Ile Thr Ile Leu Pro Gln Leu Tyr Ile Gln Pro Met Met Gly Ala
            375                 380                 385 ggc ctg aat tat gaa tgt tac cga ttc ggc att tcc cca tcc aca aat    1317
```

```
Gly Leu Asn Tyr Glu Cys Tyr Arg Phe Gly Ile Ser Pro Ser Thr Asn
            390                 395                 400 gcg ctg gtg atc ggt gcc acg gtg atg gag ggc ttc tac gtc atc ttc      1365
Ala Leu Val Ile Gly Ala Thr Val Met Glu Gly Phe Tyr Val Ile Phe
        405                 410                 415 gac aga gcc cag aag agg gtg ggc ttc gca gcg agc ccc tgt gca gaa      1413
Asp Arg Ala Gln Lys Arg Val Gly Phe Ala Ala Ser Pro Cys Ala Glu
420                 425                 430                 435 att gca ggt gct gca gtg tct gaa att tcc ggg cct ttc tca aca gag      1461
Ile Ala Gly Ala Ala Val Ser Glu Ile Ser Gly Pro Phe Ser Thr Glu
                440                 445                 450 gat gta gcc agc aac tgt gtc ccc gct cag tct ttg agc gag ccc att      1509
Asp Val Ala Ser Asn Cys Val Pro Ala Gln Ser Leu Ser Glu Pro Ile
            455                 460                 465 ttg tgg att gtg tcc tat gcg ctc atg agc gtc tgt gga gcc atc ctc      1557
Leu Trp Ile Val Ser Tyr Ala Leu Met Ser Val Cys Gly Ala Ile Leu
        470                 475                 480 ctt gtc tta atc gtc ctg ctg ctg ccg ttc cgg tgt cag cgt cgc          1605
Leu Val Leu Ile Val Leu Leu Leu Pro Phe Arg Cys Gln Arg Arg
485                 490                 495 ccc cgt gac cct gag gtc gtc aat gat gag tcc tct ctg gtc aga cat      1653
Pro Arg Asp Pro Glu Val Val Asn Asp Glu Ser Ser Leu Val Arg His
500                 505                 510                 515 cgc tgg aaa tgaatagcca ggcctgacct caagcaacca tgaactcagc              1702
Arg Trp Lys tattaagaaa atcacatttc cagggcagca gccgggatcg atggtggcgc tttctcctgt   1762
gcccacccgt cttcaatctc tgttctgctc ccagatgcct tctagattca ctgtcttttg   1822
attcttgatt ttcaagcttt caaatcctcc ctacttccaa g                        1863

<210> SEQ ID NO 2
<211> LENGTH: 518
<212> TYPE: PRT
<213> ORGANISM: Homo sapiens

<400> SEQUENCE: 2

Met Gly Ala Leu Ala Arg Ala Leu Leu Leu Pro Leu Leu Ala Gln Trp
1               5                   10                  15

Leu Leu Arg Ala Ala Pro Glu Leu Ala Pro Ala Pro Phe Thr Leu Pro
            20                  25                  30

Leu Arg Val Ala Ala Ala Thr Asn Arg Val Val Ala Pro Thr Pro Gly
        35                  40                  45

Pro Gly Thr Pro Ala Glu Arg His Ala Asp Gly Leu Ala Leu Ala Leu
    50                  55                  60

Glu Pro Ala Leu Ala Ser Pro Ala Gly Ala Ala Asn Phe Leu Ala Met
65                  70                  75                  80

Val Asp Asn Leu Gln Gly Asp Ser Gly Arg Gly Tyr Tyr Leu Glu Met
                85                  90                  95

Leu Ile Gly Thr Pro Pro Gln Lys Leu Gln Ile Leu Val Asp Thr Gly
            100                 105                 110

Ser Ser Asn Phe Ala Val Ala Gly Thr Pro His Ser Tyr Ile Asp Thr
        115                 120                 125

Tyr Phe Asp Thr Glu Arg Ser Ser Thr Tyr Arg Ser Lys Gly Phe Asp
    130                 135                 140

Val Thr Val Lys Tyr Thr Gln Gly Ser Trp Thr Gly Phe Val Gly Glu
145                 150                 155                 160

Asp Leu Val Thr Ile Pro Lys Gly Phe Asn Thr Ser Phe Leu Val Asn
```

```
                   165                 170                 175

Ile Ala Thr Ile Phe Glu Ser Glu Asn Phe Phe Leu Pro Gly Ile Lys
                180                 185                 190

Trp Asn Gly Ile Leu Gly Leu Ala Tyr Ala Thr Leu Ala Lys Pro Ser
                195                 200                 205

Ser Ser Leu Glu Thr Phe Phe Asp Ser Leu Val Thr Gln Ala Asn Ile
    210                 215                 220

Pro Asn Val Phe Ser Met Gln Met Cys Gly Ala Gly Leu Pro Val Ala
225                 230                 235                 240

Gly Ser Gly Thr Asn Gly Gly Ser Leu Val Leu Gly Gly Ile Glu Pro
                245                 250                 255

Ser Leu Tyr Lys Gly Asp Ile Trp Tyr Thr Pro Ile Lys Glu Glu Trp
                260                 265                 270

Tyr Tyr Gln Ile Glu Ile Leu Lys Leu Glu Ile Gly Gly Gln Ser Leu
                275                 280                 285

Asn Leu Asp Cys Arg Glu Tyr Asn Ala Asp Lys Ala Ile Val Asp Ser
    290                 295                 300

Gly Thr Thr Leu Leu Arg Leu Pro Gln Lys Val Phe Asp Ala Val Val
305                 310                 315                 320

Glu Ala Val Ala Arg Ala Ser Leu Ile Pro Glu Phe Ser Asp Gly Phe
                325                 330                 335

Trp Thr Gly Ser Gln Leu Ala Cys Trp Thr Asn Ser Glu Thr Pro Trp
                340                 345                 350

Ser Tyr Phe Pro Lys Ile Ser Ile Tyr Leu Arg Asp Glu Asn Ser Ser
                355                 360                 365

Arg Ser Phe Arg Ile Thr Ile Leu Pro Gln Leu Tyr Ile Gln Pro Met
370                 375                 380

Met Gly Ala Gly Leu Asn Tyr Glu Cys Tyr Arg Phe Gly Ile Ser Pro
385                 390                 395                 400

Ser Thr Asn Ala Leu Val Ile Gly Ala Thr Val Met Glu Gly Phe Tyr
                405                 410                 415

Val Ile Phe Asp Arg Ala Gln Lys Arg Val Gly Phe Ala Ala Ser Pro
                420                 425                 430

Cys Ala Glu Ile Ala Gly Ala Ala Val Ser Glu Ile Ser Gly Pro Phe
            435                 440                 445

Ser Thr Glu Asp Val Ala Ser Asn Cys Val Pro Ala Gln Ser Leu Ser
    450                 455                 460

Glu Pro Ile Leu Trp Ile Val Ser Tyr Ala Leu Met Ser Val Cys Gly
465                 470                 475                 480

Ala Ile Leu Leu Val Leu Ile Val Leu Leu Leu Pro Phe Arg Cys
                485                 490                 495

Gln Arg Arg Pro Arg Asp Pro Glu Val Val Asn Asp Glu Ser Ser Leu
                500                 505                 510

Val Arg His Arg Trp Lys
                515

<210> SEQ ID NO 3
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 3
gctacagatt ctcgttgcca ctggaagcag taactttg                          38
```

```
<210> SEQ ID NO 4
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 4
caaagttact gcttccagtg gcaacgagaa tctgtagc                              38

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Cys Leu Arg Gln Gln His Asp Asp Phe Ala Asp Asp Ile Ser Leu Leu
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Cys Gln Arg Arg Pro Arg Asp Pro Glu Val Val Asn Asp Glu Ser Ser
 1               5                  10                  15
```